US012773272B2

(12) United States Patent
Zaides et al.

(10) Patent No.: US 12,773,272 B2
(45) Date of Patent: Oct. 27, 2026

(54) USING SIGNED DISTANCE FUNCTIONS TO VISUALIZE PULSED FIELD ABLATION (PFA) TAGS

(71) Applicant: Biosense Webster (Israel) Ltd., Yokneam (IL)

(72) Inventors: Leonid Zaides, Atlit (IL); Lior Zar, Poria Illit (IL); Benjamin Cohen, Haifa (IL); Natan Sharon Katz, Atlit (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 319 days.

(21) Appl. No.: 18/426,078

(22) Filed: Jan. 29, 2024

(65) Prior Publication Data

US 2024/0245467 A1 Jul. 25, 2024

Related U.S. Application Data

(63) Continuation-in-part of application No. 18/081,486, filed on Dec. 14, 2022, now Pat. No. 12,437,466.

(51) Int. Cl.
*A61B 34/20* (2016.01)
*A61B 18/00* (2006.01)
(Continued)

(52) U.S. Cl.
CPC .............. *A61B 34/20* (2016.02); *A61B 18/00* (2013.01); *A61B 34/25* (2016.02); *A61B 90/90* (2016.02);
(Continued)

(58) Field of Classification Search
CPC ................ A61B 18/1492; A61B 18/00; A61B 2018/00351; A61B 2018/00613;
(Continued)

(56) References Cited

U.S. PATENT DOCUMENTS 4,710,876 A 12/1987 Cline et al.
5,391,199 A 2/1995 Ben-Haim
(Continued)

FOREIGN PATENT DOCUMENTS

EP 2712546 A1 4/2014
WO 2021108312 A1 6/2021
(Continued)

OTHER PUBLICATIONS

Extended European Search Report issued on May 28, 2025 for European Patent Application No. 25154316.1.
(Continued)

*Primary Examiner* — Joseph A Stoklosa
*Assistant Examiner* — Marina Delaney Templeton
(74) *Attorney, Agent, or Firm* — Volpe Koenig

(57) ABSTRACT

Disclosed are systems and methods for visualization of pulsed field ablation tags. In some implementations, a system includes a device, comprising a processor in communication with one or more sensors and a catheter comprising a plurality of electrodes. In some implementations, the processor is configured to: receive, via the one or more sensors, a position of each of the plurality of electrodes within a three-dimensional environment during a first ablation session; calculate, for the first ablation session, a first implicit function representing an energy field of the first ablation session from the received positions of each of the plurality of electrodes; and present, via a display, a first volumetric representation of the calculated first implicit function.

18 Claims, 19 Drawing Sheets
(4 of 19 Drawing Sheet(s) Filed in Color)

(51) Int. Cl.
*A61B 34/00* (2016.01)
*A61B 90/90* (2016.01)

(52) U.S. Cl.
CPC ............... *A61B 2018/00351* (2013.01); *A61B 2018/00577* (2013.01); *A61B 2018/00613* (2013.01); *A61B 2018/00839* (2013.01); *A61B 2034/2051* (2016.02)

(58) Field of Classification Search
CPC ........... A61B 2018/00839; A61B 2018/00577; A61B 2017/00053; A61B 90/90; A61B 34/20; A61B 34/25; A61B 2034/2051; A61B 2034/2053; A61B 2034/107; A61B 2034/105; A61B 2034/2072; G06T 19/20; G06T 19/00; G06T 2219/2021; G06T 2210/41
See application file for complete search history.

(56) References Cited

U.S. PATENT DOCUMENTS

| | | | | |
|---|---|---|---|---|
| 5,443,489 | A | 8/1995 | Ben-Haim | |
| 5,558,091 | A | 9/1996 | Acker et al. | |
| 6,172,499 | B1 | 1/2001 | Ashe | |
| 6,239,724 | B1 | 5/2001 | Doron et al. | |
| 6,332,089 | B1 | 12/2001 | Acker et al. | |
| 6,484,118 | B1 | 11/2002 | Govari | |
| 6,618,612 | B1 | 9/2003 | Acker et al. | |
| 6,690,963 | B2 | 2/2004 | Ben-Haim et al. | |
| 6,788,967 | B2 | 9/2004 | Ben-Haim et al. | |
| 6,892,091 | B1 | 5/2005 | Ben-Haim et al. | |
| 7,189,208 | B1 | 3/2007 | Beatty et al. | |
| 7,536,218 | B2 | 5/2009 | Govari et al. | |
| 7,756,576 | B2 | 7/2010 | Levin | |
| 7,848,787 | B2 | 12/2010 | Osadchy | |
| 7,869,865 | B2 | 1/2011 | Govari et al. | |
| 8,456,182 | B2 | 6/2013 | Bar-tal et al. | |
| 9,504,853 | B2 | 11/2016 | Sumanaweera et al. | |
| 9,700,368 | B2 | 7/2017 | Callas et al. | |
| 9,757,182 | B2 | 9/2017 | Bustan et al. | |
| 10,423,757 | B2 | 9/2019 | Kruecker et al. | |
| 2003/0078509 | A1 | 4/2003 | Panescu | |
| 2006/0241445 | A1 | 10/2006 | Altmann et al. | |
| 2007/0049821 | A1 | 3/2007 | Willis | |
| 2007/0299351 | A1 | 12/2007 | Harlev et al. | |
| 2009/0112109 | A1 | 4/2009 | Kuklik et al. | |
| 2015/0018698 | A1 | 1/2015 | Safran et al. | |
| 2015/0366481 | A1* | 12/2015 | Voth | A61B 5/287 600/523 |
| 2017/0319258 | A9 | 11/2017 | Govari et al. | |
| 2019/0043197 | A1 | 2/2019 | Adler | |
| 2020/0163569 | A1 | 5/2020 | Schwartz et al. | |
| 2021/0137588 | A1* | 5/2021 | Adawi | A61B 18/1492 |
| 2021/0401503 | A1 | 12/2021 | Harlev et al. | |
| 2023/0414275 | A1* | 12/2023 | Howard | A61B 18/1492 |
| 2024/0180616 | A1* | 6/2024 | Garrott | A61B 18/1492 |

FOREIGN PATENT DOCUMENTS

| | | | |
|---|---|---|---|
| WO | 2021/208306 | A1 | 10/2021 |
| WO | 2024127164 | A1 | 6/2024 |

OTHER PUBLICATIONS

International Search Report and Written Opinion issued on Mar. 20, 2024 mailed for PCT Patent Application No. PCT/B2023/062294.

United States Office Action issued on Feb. 14, 2025 for U.S. Appl. No. 18/081,486.

* cited by examiner

400

412

USING SIGNED DISTANCE FUNCTIONS TO VISUALIZE PULSED FIELD ABLATION (PFA) TAGS

RELATED APPLICATIONS

This application claims the benefit of and priority as a continuation-in-part to U.S. Nonprovisional patent application Ser. No. 18/081,486, entitled "Using Signed Distance Functions to Visualize Pulsed Field Ablation," filed Dec. 14, 2022, the entirety of which is incorporated by reference herein.

FIELD OF INVENTION

The present invention is related to systems and methods for tracking and visualizing invasive medical treatments. More particularly, the present invention relates to systems and methods for using signed distance functions to visualize pulsed field ablation (PFA) tags.

BACKGROUND

During pulsed field ablation (PFA), electrodes of a single-electrode catheter or multi-electrode catheter such as the VARIPULSE multi-electrode catheter manufactured by Biosense Webster, Inc. of Irvine, California are activated to damage electrical pathways in tissue by forming non-conducting lesions. During the procedure, these electrodes may be activated multiple times, with each activation sometimes referred to as an ablation session. Due to the number of activations and, for multi-electrode catheters, the number of electrodes, it may be difficult for a physician to understand the effect of an ablation session or sessions. Specifically, while the positions of the activated electrodes of the catheter may be recorded during the procedure and displayed as a point cloud or plurality of tags or markers in a three-dimensional space, such displays do not indicate the ablation field energy received by tissue. Additionally, the energy from the electric field between electrodes is not represented. This may be significant, particularly over multiple ablation sessions as energy is accumulated in the tissue. Furthermore, point cloud representations may not clearly distinguish between different ablation sessions or provide a clear indication that two points or tags were created from the same ablation session.

SUMMARY

Implementations of the systems and methods described herein address these and other problems by representing each ablation session as a combination of adjacent implicit functions. In some implementations, the energy field between adjacent electrodes may be represented by a signed distance function. In many implementations, the adjacent implicit functions are smoothly connected, improving the representability of the energy field received by a single catheter ablation session. In some implementations, the implicit functions may be rendered to a display within a three-dimensional environment via volumetric tracing. In some implementations, shading or color may be utilized to show accumulated energy across multiple ablation sessions (e.g. with darker regions indicating more accumulated energy and lighter regions indicating lower accumulated energy, or vice versa).

According to an exemplary embodiment, a system for visualization of pulsed field ablation tags is provided. In embodiments, the system includes a device, comprising a processor in communication with one or more sensors and a catheter comprising a plurality of electrodes. In embodiments, the processor is configured to: receive, via the one or more sensors, a position of each of the plurality of electrodes within a three-dimensional environment during a first ablation session; calculate, for the first ablation session, a first implicit function representing an energy field of the first ablation session from the received positions of each of the plurality of electrodes; and present, via a display, a first volumetric representation of the calculated first implicit function.

In some embodiments, the processor is further configured to calculate the first implicit function via a signed distance function based on positions of a pair of adjacent electrodes of the plurality of electrodes during the first ablation session. In a further embodiment, the processor is further configured to calculate the implicit function via a plurality of signed distance functions, each corresponding to a different pair of adjacent electrodes. In some embodiments, the processor is further configured to, for each of a plurality of voxels of the three-dimensional environment, calculate a distance from the voxel to a position of an electrode of the plurality of electrodes. In a further embodiment, the processor is further configured to, for each of the plurality of voxels of the three-dimensional environment, determine whether the corresponding calculated distance is less than a threshold. In a still further embodiment, the processor is further configured to, for one or more voxels of the plurality of voxels of the three-dimensional environment, modify a value associated with the voxel responsive to the corresponding calculated distance being less than the threshold. In another still further embodiment, the processor is further configured to modify a value associated with a first voxel, responsive to the distance from the first voxel to a position of an electrode of the plurality of electrodes during the first ablation session being less than the threshold; and modify the value associated with the first voxel, responsive to the distance from the first voxel to a position of an electrode of the plurality of electrodes during a second ablation session being less than the threshold. In yet another still further embodiment, the processor is further configured to present the first volumetric representation as one or more voxels in the three-dimensional environment, each voxel shaded based on the value associated with the voxel. In a yet still further embodiment, the processor is further configured to: receive, via the one or more sensors, a position of each of the plurality of electrodes during a second ablation session; calculate, for the second ablation session, a second implicit function representing an energy field of the second ablation session; and present, via the display, a second volumetric representation of the calculated second implicit function along with the first volumetric representation of the calculated first implicit function. In some embodiments, the processor is further configured to: sort the positions of each of the plurality of electrodes during the first ablation session into a plurality of clusters; and calculate, for the first ablation session, the first implicit function via a signed distance function between pairs of electrodes within each cluster.

In another aspect, a method for visualization of pulsed field ablation tags is provided. The method includes receiving, by a processor of a device from one or more sensors, a position within a three-dimensional environment of each of a plurality of electrodes of a catheter during a first ablation session; calculating, by the processor for the first ablation session, a first implicit function representing an energy field of the first ablation session from the received positions of each of the plurality of electrodes; and presenting, by the processor via a display, a first volumetric representation of the calculated first implicit function.

In some embodiments, the method includes calculating the first implicit function via a signed distance function based on positions of a pair of adjacent electrodes of the plurality of electrodes during the first ablation session. In a further embodiment, the method includes calculating the implicit function via a plurality of signed distance functions, each corresponding to a different pair of adjacent electrodes.

In some embodiments, the method includes calculating, for each of a plurality of voxels of the three-dimensional environment, a distance from the voxel to a position of an electrode of the plurality of electrodes. In a further embodiment, the method includes determining, for each of the plurality of voxels of the three-dimensional environment, whether the corresponding calculated distance is less than a threshold. In a still further embodiment, the method includes, for one or more voxels of the plurality of voxels of the three-dimensional environment, modifying a value associated with the voxel responsive to the corresponding calculated distance being less than the threshold. In another still further embodiment, the method includes modifying a value associated with a first voxel, responsive to the distance from the first voxel to a position of an electrode of the plurality of electrodes during the first ablation session being less than the threshold; and modifying the value associated with the first voxel, responsive to the distance from the first voxel to a position of an electrode of the plurality of electrodes during a second ablation session being less than the threshold. In yet another still further embodiment, the method includes presenting, by the processor, the first volumetric representation as one or more voxels in the three-dimensional environment, each voxel shaded based on the value associated with the voxel. In a yet still further embodiment, the method includes receiving, via the one or more sensors, a position of each of the plurality of electrodes during a second ablation session; calculating, for the second ablation session, a second implicit function representing an energy field of the second ablation session; and presenting, via the display, a second volumetric representation of the calculated second implicit function along with the first volumetric representation of the calculated first implicit function. In a further embodiment, the method includes sorting the positions of each of the plurality of electrodes during the first ablation session into a plurality of clusters; and calculating, for the first ablation session, the first implicit function via a signed distance function between pairs of electrodes within each cluster.

According to one or more embodiments, the exemplary method embodiment above can be implemented as an apparatus, a system, and/or a computer program product.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

A more detailed understanding may be had from the following description, given by way of example in conjunction with the accompanying drawings, wherein like reference numerals in the figures indicate like elements, and wherein.

DETAILED DESCRIPTION

Figure 1:
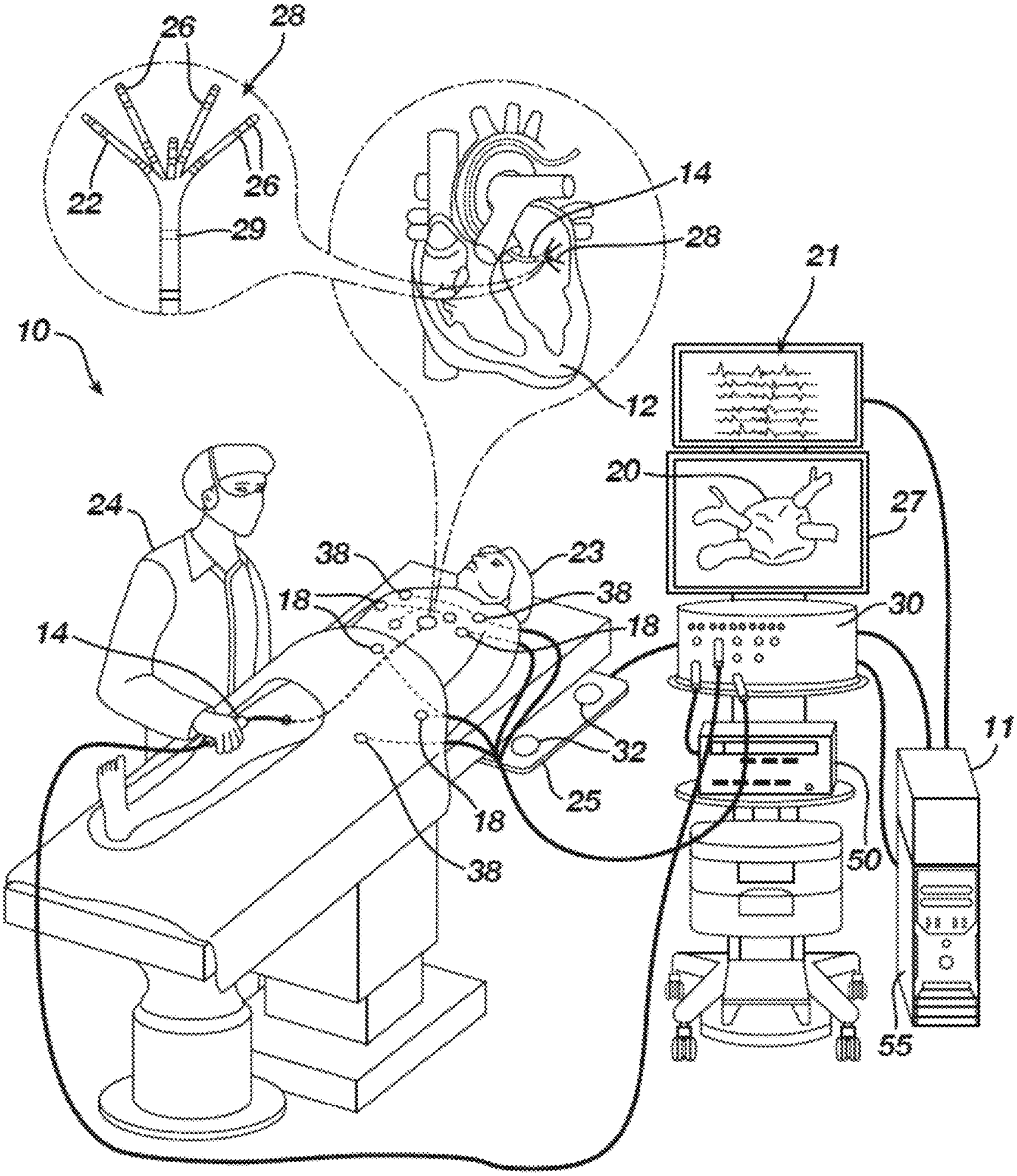
FIG. 1 depicts an example catheter-based electrophysiology mapping and ablation system according to one or more embodiments.

During pulsed field ablation (PFA), electrodes of a single-electrode catheter or multi-electrode catheter are activated to damage electrical pathways in tissue by forming non-conducting lesions. During the procedure, these electrodes may be activated multiple times, with each activation sometimes referred to as an ablation session. To provide visual feedback to a physician, some systems track the positions of the electrodes during each ablation session and provide a visualization of points or marks, sometimes referred to as tags or ablation tags, in a three-dimensional environment (e.g. representing the tissue, blood vessel, or other environment in which the catheter is placed).

Due to the number of activations and, for multi-electrode catheters, the number of electrodes, it may be difficult for a physician to understand the effect of an ablation session or sessions. In many implementations, point clouds may not identify the ablation field energy received by tissue. Additionally, the energy from the electric field between electrodes is not represented in many implementations. This may be significant, particularly over multiple ablation sessions as energy is accumulated in the tissue. Furthermore, point cloud representations may not clearly distinguish between different ablation sessions or provide a clear indication that two points or tags were created from the same ablation session.

Disclosed herein are systems and methods for visualization of pulsed field ablation tags or marks. More particularly, the present invention relates to the use of implicit functions to represent the energy field during an ablation session from a plurality of electrodes. The implicit functions may comprise a combination or aggregation of signed distance functions between adjacent pairs of electrodes in some embodiments. In many embodiments, a smooth minimum function may be used to determine energy fields between adjacent electrodes during ablation. Determining the energy fields may comprise calculating the strength or amplitude of the fields at various points in some implementations, or may comprise estimating or approximating the amplitude of the fields in other implementations. For example, in some implementations, visualization of the energy field may not require exact values and an approximation may be sufficient for use, while being faster to compute, consuming fewer resources, etc. Distances from points in the environment (e.g. represented by voxels) to one or more electrodes may be used for approximation of the energy field in many implementations.

For example, in some implementations, an energy field may be determined based on the electrode positions, and an energy threshold for which ablation may be considered sufficient may be assigned or determined. The energy field values may be converted to distances such that the distance at the provided threshold value is zero, in some implementation. Distances values may then be assigned for the relevant volume, such that energy lower than the threshold yields positive distances and higher than the threshold have negative distances. These distance values may then be easily rendered as volumetric clouds or regions within a three-dimensional environment for viewing.

In other implementations using approximations, a smooth function, such as a smooth minimum, that approximates the energy field at a given threshold may be determined. The function may be rendered as a surface, resulting in a similar visualization with significantly reduced processing requirements.

The ablation session or sessions may be rendered as a volumetric tracing within the three-dimensional environment in many implementations. Accumulated energy over multiple ablation sessions may be calculated and displayed via shading, translucence, or colors of the volumetric tracing. While many of the examples discussed herein are with respect to a heart, any anatomical structure, body part, organ, or portion thereof can be a target of ablation and visualization.

Advantageously, the implicit function requires lower processing resources and memory for rendering while still providing high quality visualizations, because for the same visual fidelity or better, the implicit function uses a smaller amount of three-dimensional data. For example, each ablation session may be represented by a single aggregate implicit function with smooth boundaries, requiring fewer resources than storing a three-dimensional bitmap or array with explicit values for each position or voxel within the environment.

Reference is made to FIG. 1 showing an example system (e.g., medical device equipment and/or catheter-based electrophysiology mapping and ablation), shown as system 10, in which one or more features of the subject matter herein can be implemented according to one or more embodiments. The system 10, as illustrated, includes a recorder 11, a heart 12, a catheter 14, a model or anatomical map 20, an electrogram 21, a spline 22, a patient 23, a physician 24 (or a medical professional or clinician), a location pad 25, an electrode 26, a display device 27, a distal tip 28, a sensor 29, a coil 32, a patient interface unit (PIU) 30, an electrode skin patches 38, an ablation energy generator 50, and a workstation 55. Note further each element and/or item of the system 10 is representative of one or more of that element and/or that item. The example of the system 10 shown in FIG. 1 can be modified to implement the embodiments disclosed herein. The disclosed embodiments can similarly be applied using other system components and settings. Additionally, the system 10 can include additional components, such as elements for sensing electrical activity, wired or wireless connectors, processing and display devices, or the like The system 10 includes multiple catheters 14, which are percutaneously inserted by the physician 24 through the patient's vascular system into a chamber or vascular structure of the heart 12. Typically, a delivery sheath catheter is inserted into the left or right atrium near a desired location in the heart 12. Thereafter, a plurality of catheters can be inserted into the delivery sheath catheter so as to arrive at the desired location. The plurality of catheters 14 may include catheters dedicated for sensing Intracardiac Electrogram (IEGM) signals, catheters dedicated for ablating and/or catheters dedicated for both sensing and ablating. The example catheter 14 that is configured for sensing IEGM is illustrated herein. The physician 24 brings the distal tip 28 of the catheter 14 into contact with the heart wall for sensing a target site in the heart 12. For ablation, the physician 24 would similarly bring a distal end of an ablation catheter to a target site for ablating.

The catheter 14 is an exemplary catheter that includes one and preferably multiple electrodes 26 optionally distributed over a plurality of splines 22 at the distal tip 28 and configured to sense the IEGM signals. The catheter 14 may additionally include the sensor 29 embedded in or near the distal tip 28 for tracking position and orientation of the distal tip 28. Optionally and preferably, position sensor 29 is a magnetic based position sensor including three magnetic coils for sensing three-dimensional (3D) position and orientation.

The sensor 29 (e.g., a position or a magnetic based position sensor) may be operated together with the location pad 25 including a plurality of magnetic coils 32 configured to generate magnetic fields in a predefined working volume. Real time position of the distal tip 28 of the catheter 14 may be tracked based on magnetic fields generated with the location pad 25 and sensed by the sensor 29. Details of the magnetic based position sensing technology are described in U.S. Pat. Nos. 5,5391,199; 5,443,489; 5,558,091; 6,172,499; 6,239,724; 6,332,089; 6,484,118; 6,618,612; 6,690,963; 6,788,967; 6,892,091.

The system 10 includes one or more electrode patches 38 positioned for skin contact on the patient 23 to establish location reference for the location pad 25 as well as impedance-based tracking of the electrodes 26. For impedance-based tracking, electrical current is directed toward the electrodes 26 and sensed at the patches 38 (e.g., electrode skin patches) so that the location of each electrode can be triangulated via the patches 38. Details of the impedance-based location tracking technology are described in U.S. Pat. Nos. 7,536,218; 7,756,576; 7,848,787; 7,869,865; and 8,456, 182, which are incorporated herein by reference.

The recorder 11 displays the electrograms 21 captured with the electrodes 18 (e.g., body surface electrocardiogram (ECG) electrodes) and intracardiac electrograms (IEGM) captured with the electrodes 26 of the catheter 14. The recorder 11 may include pacing capability for pacing the heart rhythm and/or may be electrically connected to a standalone pacer.

The system 10 may include the ablation energy generator 50 that is adapted to conduct ablative energy to the one or more of electrodes 26 at the distal tip 28 of the catheter 14 configured for ablating. Energy produced by the ablation energy generator 50 may include, but is not limited to, radiofrequency (RF) energy or pulsed-field ablation (PFA) energy, including monopolar or bipolar high-voltage DC pulses as may be used to effect irreversible electroporation (IRE), or combinations thereof.

The PIU 30 is an interface configured to establish electrical communication between catheters, electrophysiological equipment, power supply and the workstation 55 for controlling operation of the system 10. Electrophysiological equipment of the system 10 may include for example, multiple catheters 14, the location pad 25, the body surface ECG electrodes 18, the electrode patches 38, the ablation energy generator 50, and the recorder 11. Optionally and preferably, the PIU 30 additionally includes processing capability for implementing real-time computations of location of the catheters and for performing ECG calculations.

The workstation 55 includes memory, processor unit with memory or storage with appropriate operating software loaded therein, and user interface capability. The workstation 55 may provide multiple functions, optionally including (1) modeling the endocardial anatomy in three-dimensions (3D) and rendering the model or anatomical map 20 for display on the display device 27, (2) displaying on the display device 27 activation sequences (or other data) compiled from recorded electrograms 21 in representative visual indicia or imagery superimposed on the rendered anatomical map 20, (3) displaying real-time location and orientation of multiple catheters within the heart chamber, and (5) displaying on the display device 27 sites of interest such as places where ablation energy has been applied. One commercial product embodying elements of the system 10 is available as the CARTO™ 3 System, available from Biosense Webster, Inc., 31A Technology Drive, Irvine, CA 92618.

For instance, the system 10 can be part of a surgical system (e.g., CARTO® system sold by Biosense Webster) that is configured to obtain biometric data (e.g., anatomical and electrical measurements of a patient's organ, such as the heart 12 and as described herein) and perform a cardiac ablation procedure. More particularly, treatments for cardiac conditions such as cardiac arrhythmia often require obtaining a detailed mapping of cardiac tissue, chambers, veins, arteries and/or electrical pathways. For example, a prerequisite for performing a catheter ablation (as described herein) successfully is that the cause of the cardiac arrhythmia is accurately located in a chamber of the heart 12. Such locating may be done via an electrophysiological investigation during which electrical potentials are detected spatially resolved with a mapping catheter (e.g., the catheter 14) introduced into the chamber of the heart 12. This electrophysiological investigation, the so-called electro-anatomical mapping, thus provides 3D mapping data which can be displayed on the display device 27. In many cases, the mapping function and a treatment function (e.g., ablation) are provided by a single catheter or group of catheters such that the mapping catheter also operates as a treatment (e.g., ablation) catheter at the same time.

Figure 2:
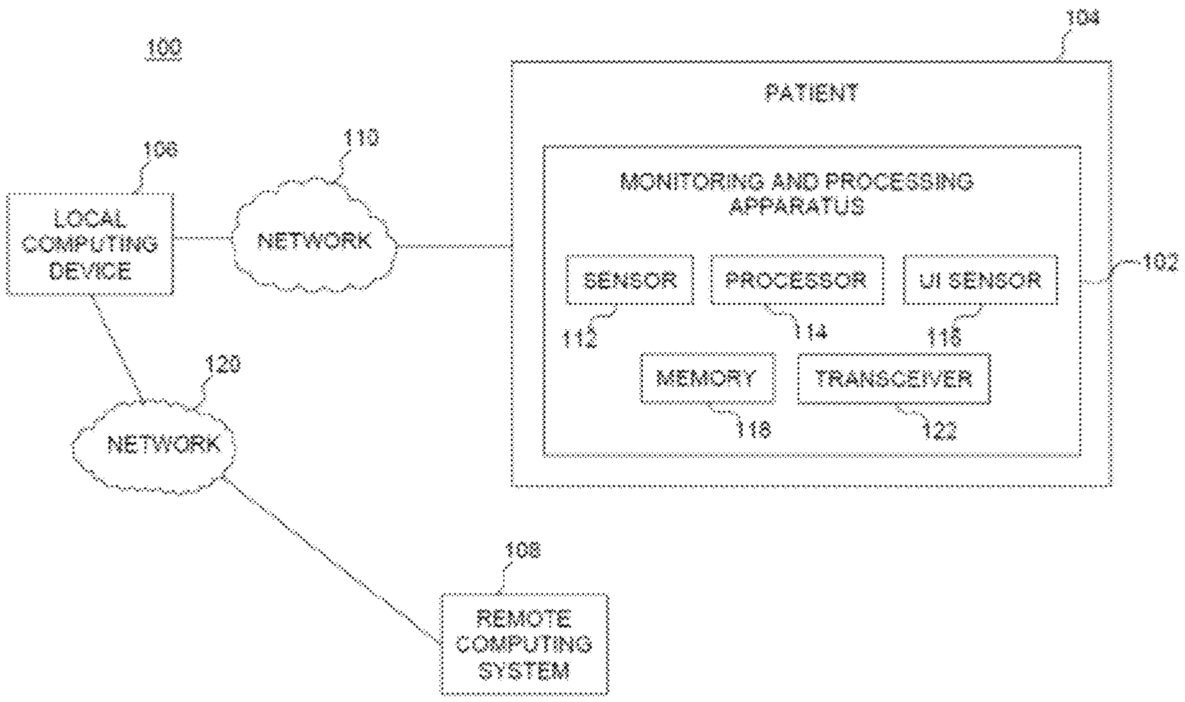
FIG. 2 is a block diagram of an example system for remotely monitoring and communicating patient biometrics according to one or more embodiments.

FIG. 2 is a block diagram of an example system 100 for remotely monitoring and communicating patient biometrics (i.e., patient data). In the example illustrated in FIG. 2, the system 100 includes a patient biometric monitoring and processing apparatus 102 associated with a patient 104, a local computing device 106, a remote computing system 108, a first network 110, a patient biometric sensor 112, a processor 114, a user input (UI) sensor 116, a memory 118, a second network 120, and a transmitter-receiver (i.e., transceiver) 122.

According to an embodiment, the patient biometric monitoring and processing apparatus 102 may be an apparatus that is internal to the patient's body (e.g., subcutaneously implantable), such as the catheter 14 of FIG. 1. The patient biometric monitoring and processing apparatus 102 may be inserted into a patient via any applicable manner including orally injecting, surgical insertion via a vein or artery, an endoscopic procedure, or a laparoscopic procedure.

According to an embodiment, the patient biometric monitoring and processing apparatus 102 may be an apparatus that is external to the patient, such as the electrode patches 38 of FIG. 1. For example, as described in more detail below, the patient biometric monitoring and processing apparatus 102 may include an attachable patch (e.g., that attaches to a patient's skin). The monitoring and processing apparatus 102 may also include a catheter with one or more electrodes, a probe, a blood pressure cuff, a weight scale, a bracelet or smart watch biometric tracker, a glucose monitor, a continuous positive airway pressure (CPAP) machine or virtually any device which may provide an input concerning the health or biometrics of the patient.

According to an embodiment, the patient biometric monitoring and processing apparatus 102 may include both components that are internal to the patient and components that are external to the patient.

The single patient biometric monitoring and processing apparatus 102 is shown in FIG. 2. Example systems may, however, may include a plurality of patient biometric monitoring and processing apparatuses. A patient biometric monitoring and processing apparatus may be in communication with one or more other patient biometric monitoring and processing apparatuses. Additionally or alternatively, a patient biometric monitoring and processing apparatus may be in communication with the network 110.

One or more patient biometric monitoring and processing apparatuses 102 may acquire patient biometric data (e.g., electrical signals, blood pressure, temperature, blood glucose level or other biometric data) and receive at least a portion of the patient biometric data representing the acquired patient biometrics and additional formation associated with acquired patient biometrics from one or more other patient biometric monitoring and processing apparatuses 102. The additional information may be, for example, diagnosis information and/or additional information obtained from an additional device such as a wearable device. Each of the patient biometric monitoring and processing apparatus 102 may process data, including its own acquired patient biometrics as well as data received from one or more other patient biometric monitoring and processing apparatuses 102.

Biometric data (e.g., patient biometrics, patient data, or patient biometric data) can include one or more of local activation times (LATs), electrical activity, topology, bipolar mapping, reference activity, ventricle activity, dominant frequency, impedance, or the like. The LAT can be a point in time of a threshold activity corresponding to a local activation, calculated based on a normalized initial starting point. Electrical activity can be any applicable electrical signals that can be measured based on one or more thresholds and can be sensed and/or augmented based on signal to noise ratios and/or other filters. A topology can correspond to the physical structure of a body part or a portion of a body part and can correspond to changes in the physical structure relative to different parts of the body part or relative to different body parts. A dominant frequency can be a frequency or a range of frequency that is prevalent at a portion of a body part and can be different in different portions of the same body part. For example, the dominant frequency of a PV of a heart can be different than the dominant frequency of the right atrium of the same heart. Impedance can be the resistance measurement at a given area of a body part.

Examples of biometric data include, but are not limited to, patient identification data, intracardiac electrocardiogram (IC ECG) data, bipolar intracardiac reference signals, anatomical and electrical measurements, trajectory information, body surface (BS) ECG data, historical data, brain biometrics, blood pressure data, ultrasound signals, radio signals, audio signals, a two- or three-dimensional image data, blood glucose data, and temperature data. The biometrics data can be used, generally, to monitor, diagnosis, and treatment any number of various diseases, such as cardiovascular diseases (e.g., arrhythmias, cardiomyopathy, and coronary artery disease) and autoimmune diseases (e.g., type I and type II diabetes). Note that BS ECG data can include data and signals collected from electrodes on a surface of a patient, IC ECG data can include data and signals collected from electrodes within the patient, and ablation data can include data and signals collected from tissue that has been ablated. Further, BS ECG data, IC ECG data, and ablation data, along with catheter electrode position data, can be derived from one or more procedure recordings.

In FIG. 2, the network 110 is an example of a short-range network (e.g., local area network (LAN), or personal area network (PAN)). Information may be sent, via the network 110, between the patient biometric monitoring and processing apparatus 102 and the local computing device 106 using any one of various short-range wireless communication protocols, such as Bluetooth, Wi-Fi, Zigbee, Z-Wave, near field communications (NFC), ultraband, Zigbee, or infrared (IR).

The network 120 may be a wired network, a wireless network or include one or more wired and wireless networks. For example, the network 120 may be a long-range network (e.g., wide area network (WAN), the internet, or a cellular network,). Information may be sent, via the network 120 using any one of various long-range wireless communication protocols (e.g., TCP/IP, HTTP, 3G, 4G/LTE, or 5G/New Radio).

The patient biometric monitoring and processing apparatus 102 may include the patient biometric sensor 112, the processor 114, the UI sensor 116, the memory 118, and the transceiver 122. The patient biometric monitoring and processing apparatus 102 may continually or periodically monitor, store, process and communicate, via the network 110, any number of various patient biometrics. Examples of patient biometrics include electrical signals (e.g., ECG signals and brain biometrics), blood pressure data, blood glucose data and temperature data. The patient biometrics may be monitored and communicated for treatment across any number of various diseases, such as cardiovascular diseases (e.g., arrhythmias, cardiomyopathy, and coronary artery disease) and autoimmune diseases (e.g., type I and type II diabetes).

The patient biometric sensor 112 may include, for example, one or more sensors configured to sense a type of biometric patient biometrics. For example, the patient biometric sensor 112 may include an electrode configured to acquire electrical signals (e.g., heart signals, brain signals or other bioelectrical signals), a temperature sensor, a blood pressure sensor, a blood glucose sensor, a blood oxygen sensor, a pH sensor, an accelerometer and a microphone.

As described in more detail below, the patient biometric monitoring and processing apparatus 102 may be an ECG monitor for monitoring ECG signals of a heart (e.g., the heart 12). The patient biometric sensor 112 of the ECG monitor may include one or more electrodes for acquiring ECG signals. The ECG signals may be used for treatment of various cardiovascular diseases.

In another example, the patient biometric monitoring and processing apparatus 102 may be a continuous glucose monitor (CGM) for continuously monitoring blood glucose levels of a patient on a continual basis for treatment of various diseases, such as type I and type II diabetes. The CGM may include a subcutaneously disposed electrode, which may monitor blood glucose levels from interstitial fluid of the patient. The CGM may be, for example, a component of a closed-loop system in which the blood glucose data is sent to an insulin pump for calculated delivery of insulin without user intervention.

The transceiver 122 may include a separate transmitter and receiver. Alternatively, the transceiver 122 may include a transmitter and receiver integrated into a single device.

The processor 114 may be configured to store patient data, such as patient biometric data in the memory 118 acquired by the patient biometric sensor 112, and communicate the patient data, across the network 110, via a transmitter of the transceiver 122. Data from one or more other patient biometric monitoring and processing apparatus 102 may also be received by a receiver of the transceiver 122, as described in more detail below.

According to an embodiment, the patient biometric monitoring and processing apparatus 102 includes UI sensor 116 which may be, for example, a piezoelectric sensor or a capacitive sensor configured to receive a user input, such as a tapping or touching. For example, the UI sensor 116 may be controlled to implement a capacitive coupling, in response to tapping or touching a surface of the patient biometric monitoring and processing apparatus 102 by the patient 104. Gesture recognition may be implemented via any one of various capacitive types, such as resistive capacitive, surface capacitive, projected capacitive, surface acoustic wave, piezoelectric and infra-red touching. Capacitive sensors may be disposed at a small area or over a length of the surface such that the tapping or touching of the surface activates the monitoring device.

As described in more detail below, the processor 114 may be configured to respond selectively to different tapping patterns of the capacitive sensor (e.g., a single tap or a double tap), which may be the UI sensor 116, such that different tasks of the patch (e.g., acquisition, storing, or transmission of data) may be activated based on the detected pattern. In some embodiments, audible feedback may be given to the user from the patient biometric monitoring and processing apparatus 102 when a gesture is detected.

The local computing device 106 of the system 100 is in communication with the patient biometric monitoring and processing apparatus 102 and may be configured to act as a gateway to the remote computing system 108 through the second network 120. The local computing device 106 may be, for example, a, smart phone, smartwatch, tablet or other portable smart device configured to communicate with other devices via the network 120. Alternatively, the local computing device 106 may be a stationary or standalone device, such as a stationary base station including, for example, modem and/or router capability, a desktop or laptop computer using an executable program to communicate information between the patient biometric monitoring and processing apparatus 102 and the remote computing system 108 via the PC's radio module, or a USB dongle. Patient biometrics may be communicated between the local computing device 106 and the patient biometric monitoring and processing apparatus 102 using a short-range wireless technology standard (e.g., Bluetooth, Wi-Fi, ZigBee, Z-wave and other short-range wireless standards) via the short-range wireless network 110, such as a local area network (LAN) (e.g., a personal area network (PAN). In some embodiments, the local computing device 106 may also be configured to display the acquired patient electrical signals and information associated with the acquired patient electrical signals, as described in more detail below.

In some embodiments, the remote computing system 108 may be configured to receive at least one of the monitored patient biometrics and information associated with the monitored patient via network 120, which is a long-range network. For example, if the local computing device 106 is a mobile phone, network 120 may be a wireless cellular network, and information may be communicated between the local computing device 106 and the remote computing system 108 via a wireless technology standard, such as any of the wireless technologies mentioned above. As described in more detail below, the remote computing system 108 may be configured to provide (e.g., visually display and/or aurally provide) the at least one of the patient biometrics and the associated information to a healthcare professional (e.g., a physician).

Figure 3:
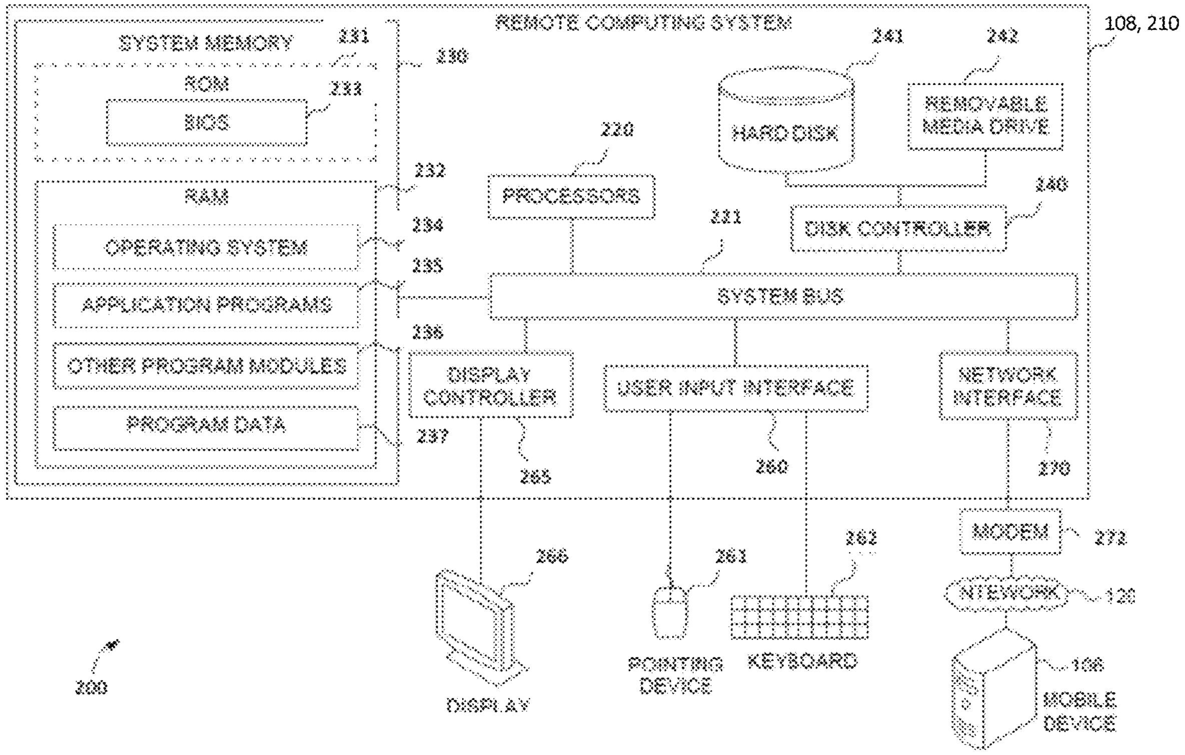
FIG. 3 is a system diagram of an example of a computing environment in communication with network according to one or more embodiments.

FIG. 3 is a system diagram of an example of a computing environment 200 in communication with network 120. In some instances, the computing environment 200 is incorporated in a public cloud computing platform (such as Amazon Web Services or Microsoft Azure), a hybrid cloud computing platform (such as HP Enterprise OneSphere) or a private cloud computing platform.

As shown in FIG. 3, computing environment 200 includes remote computing system 108 (hereinafter computer system), which is one example of a computing system upon which embodiments described herein may be implemented.

The remote computing system 108 may, via processors 220, which may include one or more processors, perform various functions. The functions may include analyzing monitored patient biometrics and the associated information and, according to physician-determined or algorithm driven thresholds and parameters, providing (e.g., via display 266) alerts, additional information or instructions. As described in more detail below, the remote computing system 108 may be used to provide (e.g., via display 266) healthcare personnel (e.g., a physician) with a dashboard of patient information, such that such information may enable healthcare personnel to identify and prioritize patients having more critical needs than others.

As shown in FIG. 3, the computer system 210 may include a communication mechanism such as a bus 221 or other communication mechanism for communicating information within the computer system 210. The computer system 210 further includes one or more processors 220 coupled with the bus 221 for processing the information. The processors 220 may include one or more CPUs, GPUs, or any other processor known in the art.

The computer system 210 also includes a system memory 230 coupled to the bus 221 for storing information and instructions to be executed by processors 220. The system memory 230 may include computer readable storage media in the form of volatile and/or nonvolatile memory, such as read only system memory (ROM) 231 and/or random-access memory (RAM) 232. The system memory RAM 232 may include other dynamic storage device(s) (e.g., dynamic RAM, static RAM, and synchronous DRAM). The system memory ROM 231 may include other static storage device (s) (e.g., programmable ROM, erasable PROM, and electrically erasable PROM). In addition, the system memory 230 may be used for storing temporary variables or other intermediate information during the execution of instructions by the processors 220. A basic input/output system 233 (BIOS) may contain routines to transfer information between elements within computer system 210, such as during start-up, that may be stored in system memory ROM 231. RAM 232 may comprise data and/or program modules that are immediately accessible to and/or presently being operated on by the processors 220. System memory 230 may additionally include, for example, operating system 234, application programs 235, other program modules 236 and program data 237.

The illustrated computer system 210 also includes a disk controller 240 coupled to the bus 221 to control one or more storage devices for storing information and instructions, such as a magnetic hard disk 241 and a removable media drive 242 (e.g., floppy disk drive, compact disc drive, tape drive, and/or solid state drive). The storage devices may be added to the computer system 210 using an appropriate device interface (e.g., a small computer system interface (SCSI), integrated device electronics (IDE), Universal Serial Bus (USB), or FireWire).

The computer system 210 may also include a display controller 265 coupled to the bus 221 to control a monitor or display 266, such as a cathode ray tube (CRT) or liquid crystal display (LCD), for displaying information to a computer user. The illustrated computer system 210 includes a user input interface 260 and one or more input devices, such as a keyboard 262 and a pointing device 261, for interacting with a computer user and providing information to the processor 220. The pointing device 261, for example, may be a mouse, a trackball, or a pointing stick for communicating direction information and command selections to the processor 220 and for controlling cursor movement on the display 266. The display 266 may provide a touch screen interface that may allow input to supplement or replace the communication of direction information and command selections by the pointing device 261 and/or keyboard 262.

The computer system 210 may perform a portion or each of the functions and methods described herein in response to the processors 220 executing one or more sequences of one or more instructions contained in a memory, such as the system memory 230. Such instructions may be read into the system memory 230 from another computer readable medium, such as a hard disk 241 or a removable media drive 242. The hard disk 241 may contain one or more data stores and data files used by embodiments described herein. Data store contents and data files may be encrypted to improve security. The processors 220 may also be employed in a multi-processing arrangement to execute the one or more sequences of instructions contained in system memory 230. In alternative embodiments, hard-wired circuitry may be used in place of or in combination with software instructions. Thus, embodiments are not limited to any specific combination of hardware circuitry and software.

As stated above, the computer system 210 may include at least one computer readable medium or memory for holding instructions programmed according to embodiments described herein and for containing data structures, tables, records, or other data described herein. The term computer readable medium as used herein refers to any non-transitory, tangible medium that participates in providing instructions to the processor 220 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 241 or removable media drive 242. Non-limiting examples of volatile media include dynamic memory, such as system memory 230. Non-limiting examples of transmission media include coaxial cables, copper wire, and fiber optics, including the wires that make up the bus 221. Transmission media may also take the form of acoustic or light waves, such as those generated during radio wave and infrared data communications.

The computing environment 200 may further include the computer system 210 operating in a networked environment using logical connections to local computing device 106 and one or more other devices, such as a personal computer (laptop or desktop), mobile devices (e.g., patient mobile devices), a server, a router, a network PC, a peer device or other common network node, and typically includes many or all of the elements described above relative to computer system 210. When used in a networking environment, computer system 210 may include modem 272 for establishing communications over a network 120, such as the Internet. Modem 272 may be connected to system bus 221 via network interface 270, or via another appropriate mechanism.

Network 120, as shown in FIGS. 2 and 3, may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 210 and other computers (e.g., local computing device 106).

Cardiac arrhythmias, and atrial fibrillation in particular, persist as common and dangerous medical ailments, especially in the aging population. In patients with normal sinus rhythm, the heart, which is comprised of atrial, ventricular, and excitatory conduction tissue, is electrically excited to beat in a synchronous, patterned fashion. In patients with cardiac arrythmias, abnormal regions of cardiac tissue do not follow the synchronous beating cycle associated with normally conductive tissue as in patients with normal sinus rhythm. Instead, the abnormal regions of cardiac tissue aberrantly conduct to adjacent tissue, thereby disrupting the cardiac cycle into an asynchronous cardiac rhythm. Such abnormal conduction has been previously known to occur at various regions of the heart, for example, in the region of the sino-atrial (SA) node, along the conduction pathways of the atrioventricular (AV) node and the Bundle of His, or in the cardiac muscle tissue forming the walls of the ventricular and atrial cardiac chambers.

Cardiac arrhythmias, including atrial arrhythmias, may be of a multiwavelet reentrant type, characterized by multiple asynchronous loops of electrical impulses that are scattered about the atrial chamber and are often self-propagating. Alternatively, or in addition to the multiwavelet reentrant type, cardiac arrhythmias may also have a focal origin, such as when an isolated region of tissue in an atrium fires autonomously in a rapid, repetitive fashion. Ventricular tachycardia (V-tach or VT) is a tachycardia, or fast heart rhythm that originates in one of the ventricles of the heart. This is a potentially life-threatening arrhythmia because it may lead to ventricular fibrillation and sudden death.

One type of arrhythmia, atrial fibrillation, occurs when the normal electrical impulses generated by the sinoatrial node are overwhelmed by disorganized electrical impulses that originate in the atria and pulmonary veins causing irregular impulses to be conducted to the ventricles. An irregular heartbeat results and may last from minutes to weeks, or even years. Atrial fibrillation (AF) is often a chronic condition that leads to a small increase in the risk of death often due to strokes. Risk increases with age. Approximately 8% of people over 80 having some amount of AF. Atrial fibrillation is often asymptomatic and is not in itself generally life-threatening, but it may result in palpitations, weakness, fainting, chest pain and congestive heart failure. Stroke risk increases during AF because blood may pool and form clots in the poorly contracting atria and the left atrial appendage. The first line of treatment for AF is medication that either slow the heart rate or revert the heart rhythm back to normal. Additionally, persons with AF are often given anticoagulants to protect them from the risk of stroke. The use of such anticoagulants comes with its own risk of internal bleeding. In some patients, medication is not sufficient and their AF is deemed to be drug-refractory, i.e., untreatable with standard pharmacological interventions. Synchronized electrical cardioversion may also be used to convert AF to a normal heart rhythm. Alternatively, AF patients are treated by catheter ablation.

A catheter ablation based treatment may include mapping the electrical properties of heart tissue, especially the endocardium and the heart volume, and selectively ablating cardiac tissue by application of energy. Cardiac mapping, for example, creating a map of electrical potentials (a voltage map) of the wave propagation along the heart tissue or a map of arrival times (a local time activation (LAT) map) to various tissue located points, may be used for detecting local heart tissue dysfunction Ablations, such as those based on cardiac mapping, can cease or modify the propagation of unwanted electrical signals from one portion of the heart to another.

The ablation process damages the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. In a two-step procedure-mapping followed by ablation-electrical activity at points within the heart is typically sensed and measured by advancing a catheter containing one or more electrical sensors (or electrodes) into the heart, and acquiring data at a multiplicity of points. These data are then utilized to select the endocardial target areas at which ablation is to be performed.

Cardiac ablation and other cardiac electrophysiological procedures have become increasingly complex as clinicians treat challenging conditions such as atrial fibrillation and ventricular tachycardia. The treatment of complex arrhythmias can now rely on the use of three dimensional (3D) mapping systems in order to reconstruct the anatomy of the heart chamber of interest.

For example, cardiologists rely upon software such as the Complex Fractionated Atrial Electrograms (CFAE) module of the CARTO® 3 3D mapping system, produced by Biosense Webster, Inc. (Diamond Bar, Calif.), to analyze intracardiac EGM signals and determine the ablation points for treatment of a broad range of cardiac conditions, including atypical atrial flutter and ventricular tachycardia.

The 3D maps, sometimes referred to as electroanatomical maps, can provide multiple pieces of information regarding the electrophysiological properties of the tissue that represent the anatomical and functional substrate of these challenging arrhythmias.

Cardiomyopathies with different etiologies (ischemic, dilated cardiomyopathy (DCM), hypertrophic cardiomyopathy (HCM), arrhythmogenic right ventricular dysplasia (ARVD), left ventricular non-compaction (LVNC), etc.) have an identifiable substrate, featured by areas of unhealthy tissue surrounded by areas of normally functioning cardiomyocytes.

Figure 4A:
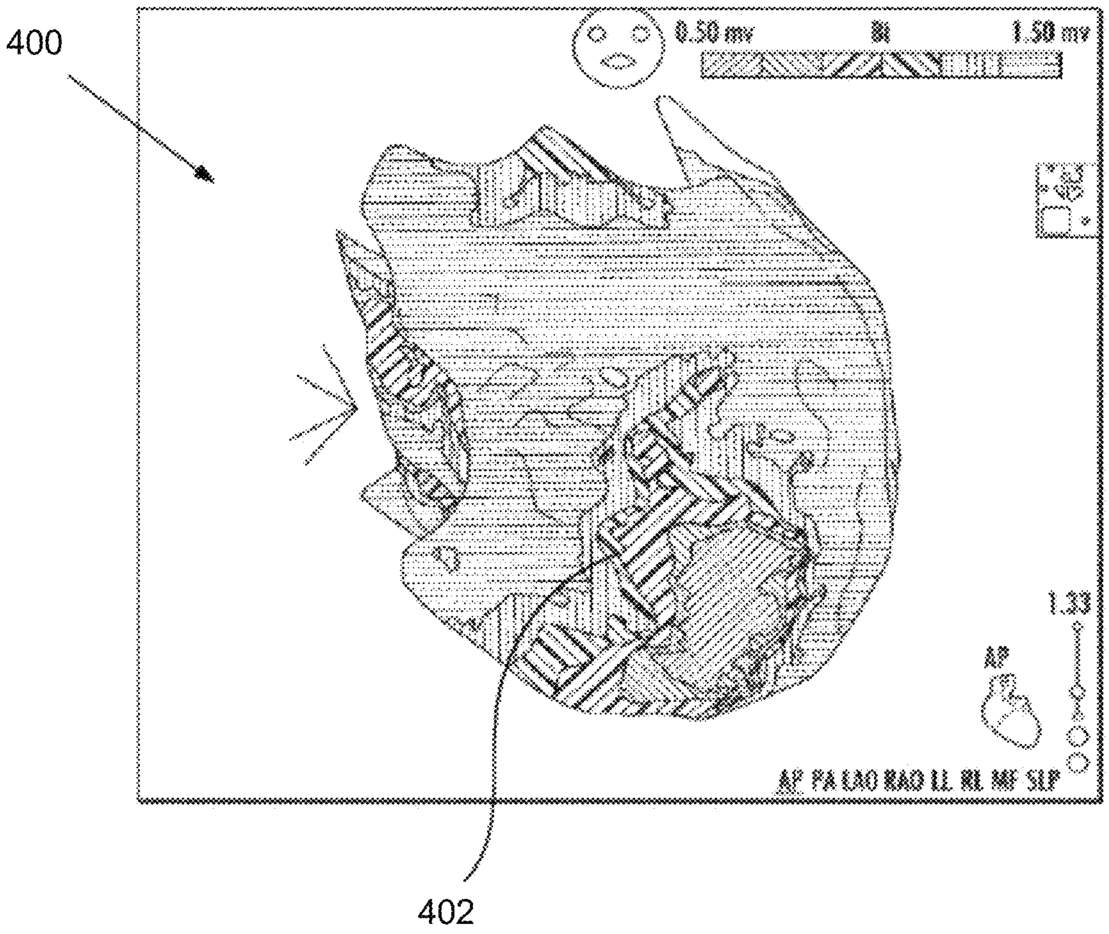
FIGS. 4A-4D are illustrations of example electroanatomical maps of cardiomyopathies.
Figure 4B:
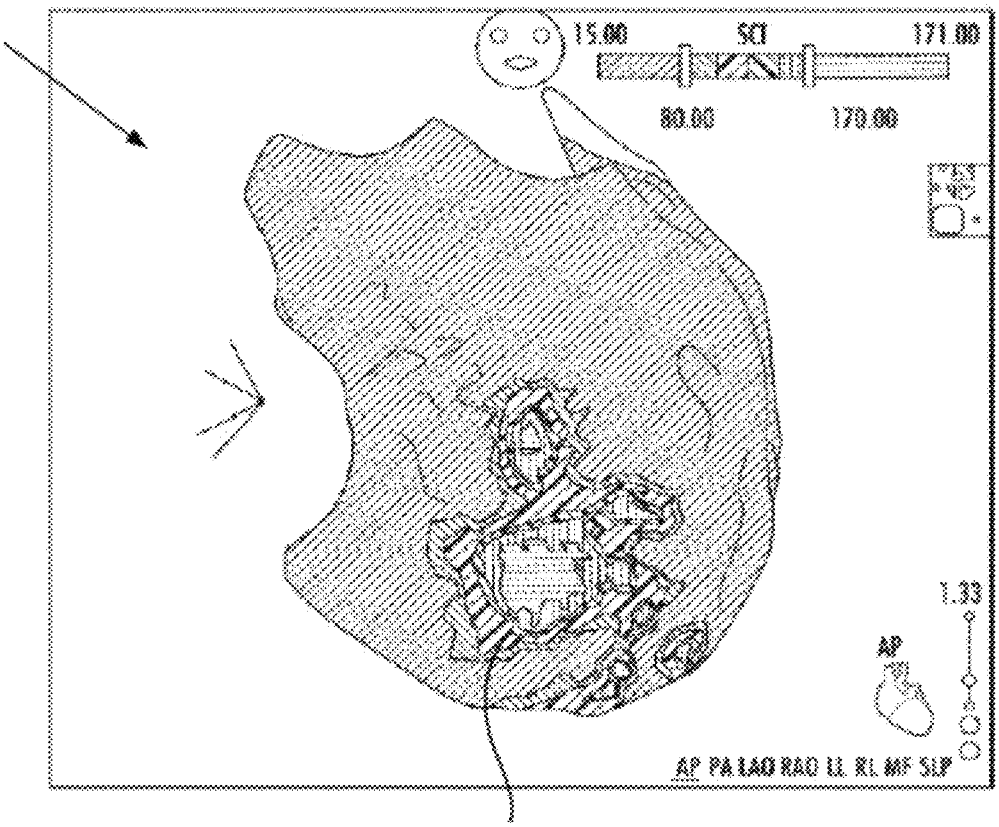

FIGS. 4A through 4D show electroanatomical map examples of cardiomyopathies with different etiologies. As a first example, FIGS. 4A and 4B show an example rendering of a heart 400 with post-ischemic Ventricular Tachycardia (VT) characterized by endo-epicardial low or intermediate voltage area 402 in which signal conduction is slowed down. This illustrates that measuring any prolonged potential inside or around the dense scar area may help identify potential isthmuses sustaining VT. The post-ischemic VT shown in FIG. 4A is characterized by an endo-epicardial low or intermediate voltage area in which signal conduction is slowed down. This illustrates that measuring any prolonged potential inside or around the dense scar area may help identify potential isthmuses sustaining VT. FIG. 4A illustrates the bipolar signal amplitude (Bi) variance in the various sectors of the heart 400. FIG. 4A shows Bi ranges from 0.5 mV to 1.5 mV. FIG. 4B illustrates the Shortex Complex Interval (SCI) variance in the various sectors of the heart. As an example, SCI ranges from 15.0 msec to 171.00 msec with the SCI range of interest between 80 msec and 170 msec.

Figure 4C:
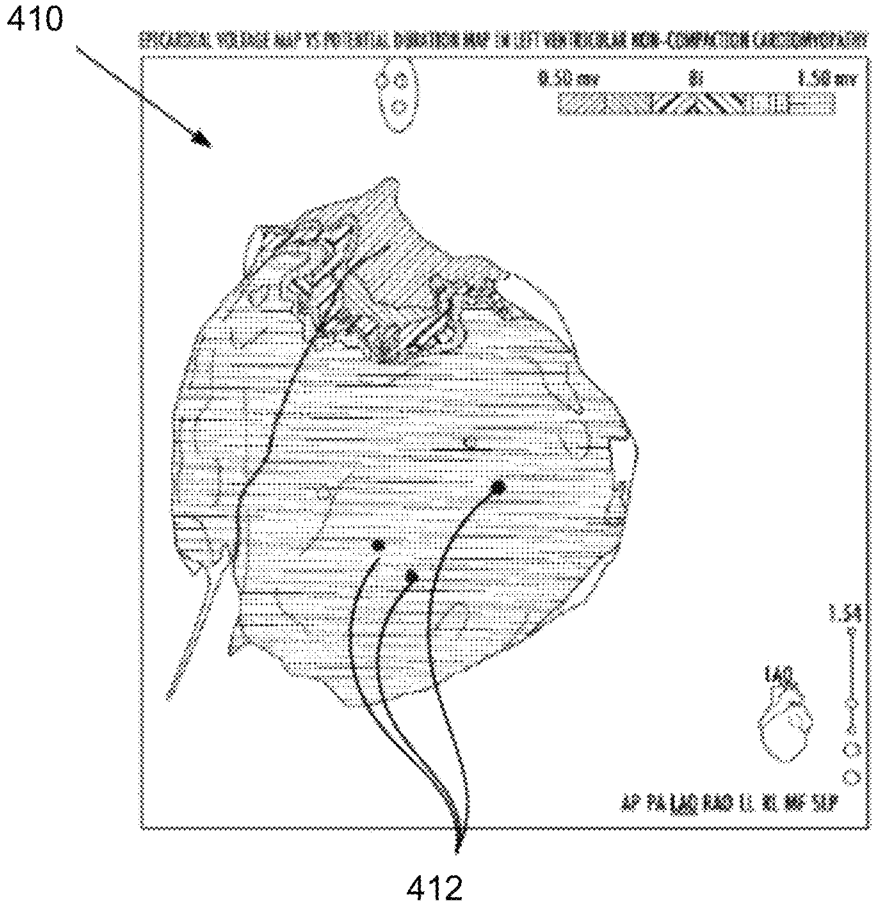
Figure 4D:
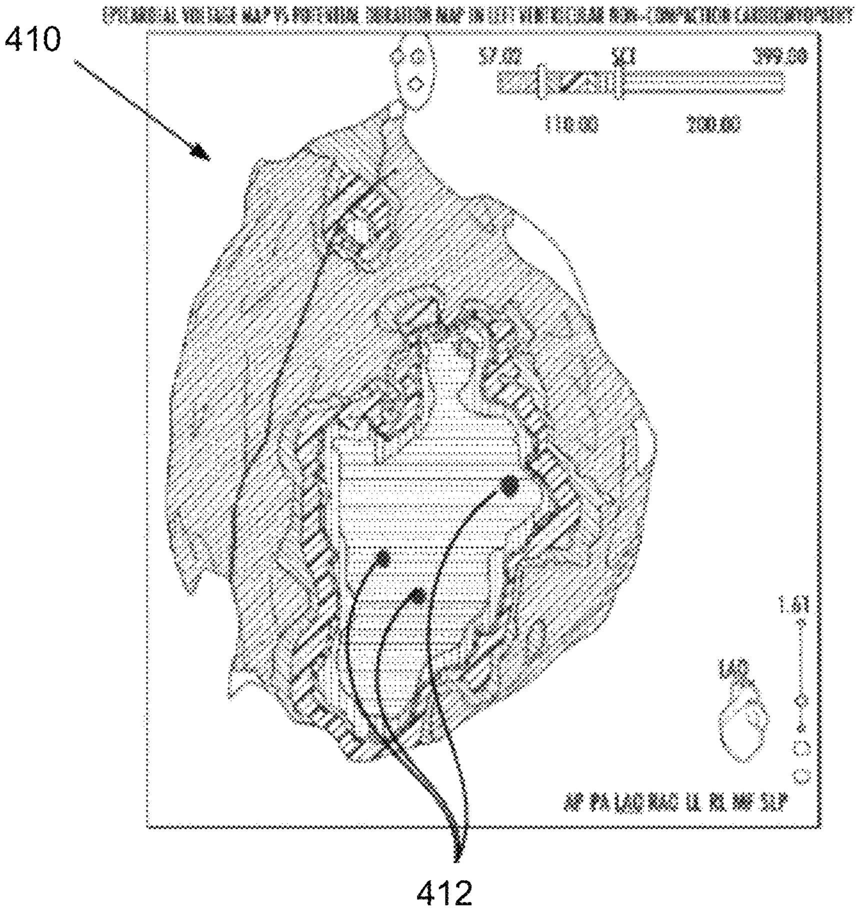

FIGS. 4C and 4D show an example rendering of a heart 410 experiencing left ventricular non-compaction cardiomyopathy. More specifically, FIG. 4C shows an epicardial voltage map and FIG. 4D shows potential duration map (PDM). The three black circles in 412 in FIGS. 4C and 4D are marked as abnormally prolonged potentials, e.g., potentials above 200 msec.

Abnormal tissue is generally characterized by low-voltage EGMs. However, initial clinical experience in endo-epicardial mapping indicates that areas of low-voltage are not always present as the sole arrhythmogenic mechanism in such patients. In fact, areas of low or medium-voltage may exhibit EGM fragmentation and prolonged activities during sinus rhythm, which corresponds to the critical isthmus identified during sustained and organized ventricular arrhythmias, e.g., applies only to non-tolerated ventricular tachycardias. Moreover, in many cases, EGM fragmentation and prolonged activities are observed in the regions showing a normal or near-normal voltage amplitude (>1-1.5 mV). Although the latter areas may be evaluated according to the voltage amplitude, they cannot be considered as normal according to the intracardiac signal, thus representing a true arrhythmogenic substrate. The 3D mapping may be able to localize the arrhythmogenic substrate on the endocardial and/or epicardial layer of the right/left ventricle, which may vary in distribution according to the extension of the main disease.

The substrate linked to these cardiac conditions is related to the presence of fragmented and prolonged EGMs in the endocardial and/or epicardial layers of the ventricular chambers (right and left). The 3D mapping system, such as CARTO® 3, is able to localize the potential arrhythmogenic substrate of the cardiomyopathy in terms of abnormal EGM detection.

Electrode catheters have been in common use in medical practice for many years. They are used to stimulate and map electrical activity in the heart and to ablate sites of aberrant electrical activity. In use, the electrode catheter is inserted into a major vein or artery, e.g., femoral artery, and then guided into the chamber of the heart of concern. A typical ablation procedure involves the insertion of a catheter having at least one electrode at its distal end, into a heart chamber. A reference electrode is provided, generally taped to the skin of the patient or by means of a second catheter that is positioned in or near the heart. RF (radio frequency) current and/or pulsed-field energy is applied to the tip electrode of the ablating catheter, and current flows through the media that surrounds it, i.e., blood and tissue, toward the reference electrode. In RF ablation, the distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive. During this process, heating of the electrode also occurs as a result of conduction from the heated tissue to the electrode itself. If the electrode temperature becomes sufficiently high, possibly above 60 degrees C., a thin transparent coating of dehydrated blood protein can form on the surface of the electrode. If the temperature continues to rise, this dehydrated layer can become progressively thicker resulting in blood coagulation on the electrode surface. Because dehydrated biological material has a higher electrical resistance than endocardial tissue, impedance to the flow of electrical energy into the tissue also increases. If the impedance increases sufficiently, an impedance rise occurs and the catheter must be removed from the body and the tip electrode cleaned. Similarly, in PFA, size, depth, and effectiveness of cardiac lesions produced by the ablation depends upon the proximity of the electrode(s) to the tissue. The electric fields generated during PFA create irreversible electroporation in the cells of the heart tissue. This process disrupts cell membranes, leading to cell death.

Treatments for cardiac conditions such as cardiac arrhythmia often require obtaining a detailed mapping of cardiac tissue, chambers, veins, arteries and/or electrical pathways. For example, a prerequisite for performing a catheter ablation successfully is that the cause of the cardiac arrhythmia is accurately located in the heart chamber. Such locating may be done via an electrophysiological investigation during which electrical potentials are detected spatially resolved with a mapping catheter introduced into the heart chamber. This electrophysiological investigation, the so-called electro-anatomical mapping, thus provides 3D mapping data which can be displayed on a monitor. In many cases, the mapping function and a treatment function (e.g., ablation) are provided by a single catheter or group of catheters such that the mapping catheter also operates as a treatment (e.g., ablation) catheter at the same time Mapping of cardiac areas such as cardiac regions, tissue, veins, arteries and/or electrical pathways of the heart may result in identifying problem areas such as scar tissue, arrythmia sources (e.g., electric rotors), healthy areas, and the like. Cardiac areas may be mapped such that a visual rendering of the mapped cardiac areas is provided using a display, as further disclosed herein. Additionally, cardiac mapping may include mapping based on one or more modalities such as, but not limited to local activation time (LAT), an electrical activity, a topology, a bipolar mapping, a dominant frequency, or an impedance. Data corresponding to multiple modalities may be captured using a catheter inserted into a patient's body and may be provided for rendering at the same time or at different times based on corresponding settings and/or preferences of a medial professional.

Cardiac mapping may be implemented using one or more techniques. As an example of a first technique, cardiac mapping may be implemented by sensing an electrical property of heart tissue, for example, local activation time, as a function of the precise location within the heart. The corresponding data may be acquired with one or more catheters that are advanced into the heart using catheters that have electrical and location sensors in their distal tips. As specific examples, location and electrical activity may be initially measured on about 10 to about 20 points on the interior surface of the heart. These data points may be generally sufficient to generate a preliminary reconstruction or map of the cardiac surface to a satisfactory quality. The preliminary map may be combined with data taken at additional points in order to generate a more comprehensive map of the heart's electrical activity. In clinical settings, it is not uncommon to accumulate data at 100 or more sites to generate a detailed, comprehensive map of heart chamber electrical activity. The generated detailed map may then serve as the basis for deciding on a therapeutic course of action, for example, tissue ablation, to alter the propagation of the heart's electrical activity and to restore normal heart rhythm.

Catheters containing position sensors may be used to determine the trajectory of points on the cardiac surface. These trajectories may be used to infer motion characteristics such as the contractility of the tissue. Maps depicting such motion characteristics may be constructed when the trajectory information is sampled at a sufficient number of points in the heart.

Electrical activity at a point in the heart may be typically measured by advancing a catheter containing an electrical sensor at or near its distal tip to that point in the heart, contacting the tissue with the sensor and acquiring data at that point. One drawback with mapping a cardiac chamber using a catheter containing only a single, distal tip electrode is the long period of time required to accumulate data on a point-by-point basis over the requisite number of points required for a detailed map of the chamber as a whole. Accordingly, multiple-electrode catheters have been developed to simultaneously measure electrical activity at multiple points in the heart chamber.

Figure 5A:
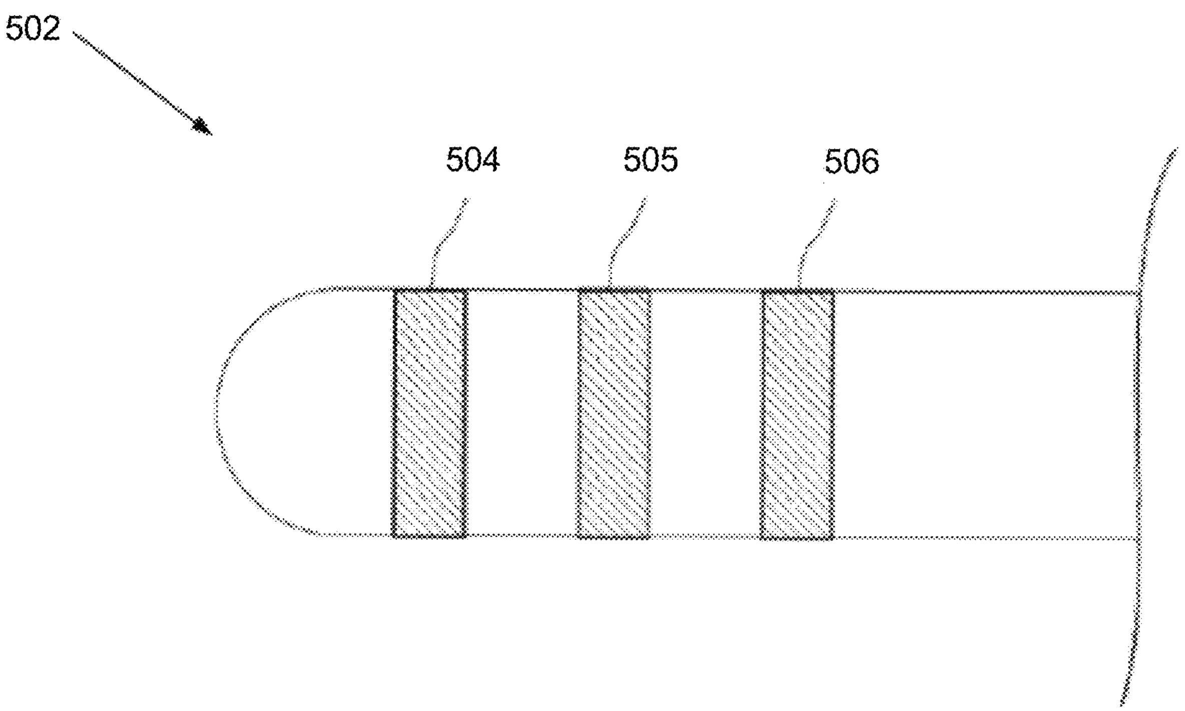
FIG. 5A depicts an example of a linear catheter including multiple electrodes according to one or more embodiments.

Multiple-electrode catheters may be implemented using any applicable shape such as a linear catheter with multiple electrodes, a balloon catheter including electrodes dispersed on multiple spines that shape the balloon, a lasso or loop catheter with multiple electrodes, or any other applicable shape. FIG. 5A shows an example of a linear catheter 502 including multiple electrodes 504, 505, and 506 that may be used to map a cardiac area. Linear catheter 502 may be fully or partially elastic such that it can twist, bend, and or otherwise change its shape based on received signal and/or based on application of an external force (e.g., cardiac tissue) on the linear catheter 502.

Figure 5B:
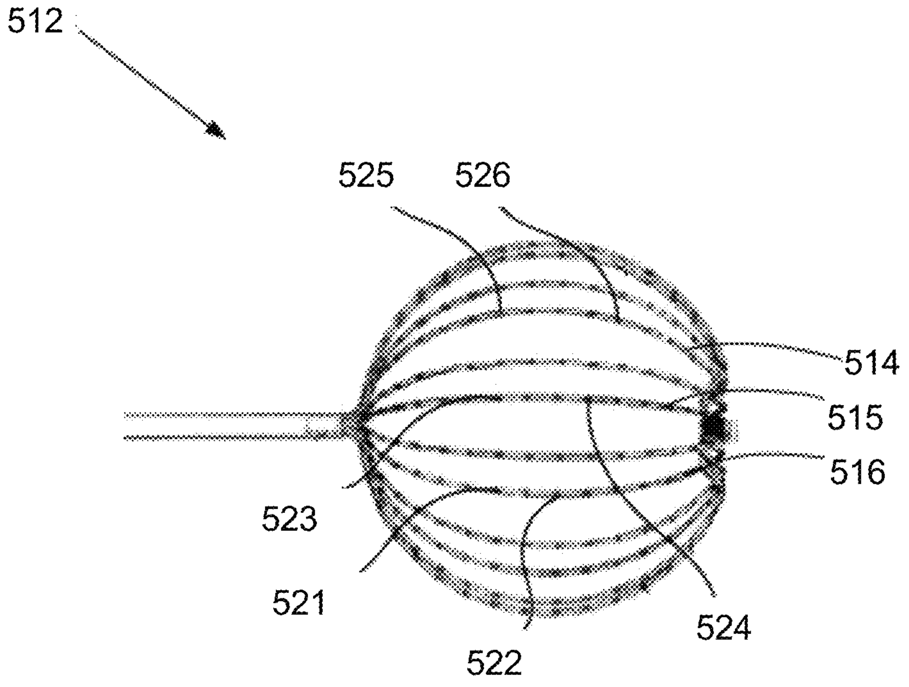
FIG. 5B depicts an example of a balloon catheter with multiple electrodes according to one or more embodiments.

FIG. 5B shows an example of a balloon catheter 512 including multiple splines (e.g., 12 splines in the specific example of FIG. 5B) including splines 514, 516, 517 and multiple electrodes on each spline including electrodes 521, 522, 523, 524, 525, and 526 as shown. The balloon catheter 512 may be designed such that when deployed into a patient's body, its electrodes may be held in intimate contact against an endocardial surface. As an example, a balloon catheter may be inserted into a lumen, such as a pulmonary vein (PV). The balloon catheter may be inserted into the PV in a deflated state such that the balloon catheter does not occupy its maximum volume while being inserted into the PV. The balloon catheter may expand while inside the PV such that electrodes on the balloon catheter are in contact with an entire circular section of the PV. Such contact with an entire circular section of the PV, or any other lumen, may enable efficient mapping and/or ablation.

Figure 5C:
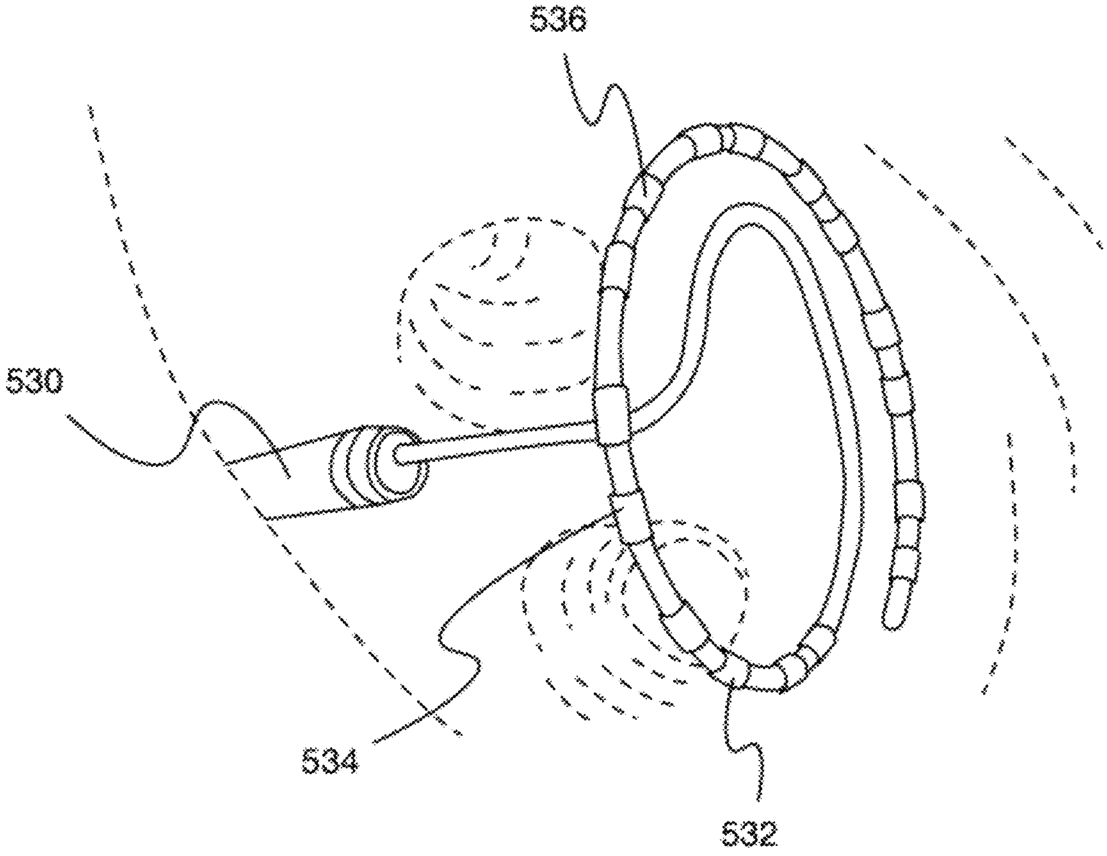
FIG. 5C depicts an example of a loop catheter with multiple electrodes according to one or more embodiments.

FIG. 5C shows an example of a loop catheter 530 (also referred to as a lasso catheter) including multiple electrodes 532, 534, and 536 that may be used to map a cardiac area. Loop catheter 530 may be fully or partially elastic such that it can twist, bend, and or otherwise change its shape based on received signal and/or based on application of an external force (e.g., cardiac tissue) on the loop catheter 530.

According to an example, a multi-electrode catheter may be advanced into a chamber of the heart. Navigation capabilities of the 3D mapping systems, such as CARTO®, may be used to establish the position and orientation of the catheter and its electrodes. This capability may be enabled via one or more location sensors (e.g., one or both of magnetic- and impedance-based sensors). Additionally or alternatively, imaging techniques such as intracardiac echocardiography (ICE) or anteroposterior (AP) and lateral fluorograms may be obtained to establish the position and orientation of each of the electrodes. Electrograms may be recorded from each of the electrodes in contact with a cardiac surface relative to a temporal reference such as the onset of the P-wave in sinus rhythm from a body surface ECG. The system, as further disclosed herein, may differentiate between those electrodes that register electrical activity and those that do not due to absence of close proximity to the endocardial wall. After initial electrograms are recorded, the catheter may be repositioned, and fluorograms and electrograms may be recorded again. An electrical map may then be constructed from iterations of the process above. In addition, intracardiac ECG data may be gathered by one or more diagnostic catheters placed inside the heart.

According to an example, cardiac mapping may be generated based on detection of intracardiac electrical potential fields. A non-contact technique to simultaneously acquire a large amount of cardiac electrical information may be implemented. For example, a catheter having a distal end portion may be provided with a series of sensor electrodes distributed over its surface and connected to insulated electrical conductors for connection to signal sensing and processing means. The size and shape of the end portion may be such that the electrodes are spaced substantially away from the wall of the cardiac chamber. Intracardiac potential fields may be detected during a single cardiac beat. According to an example, the sensor electrodes may be distributed on a series of circumferences lying in planes spaced from each other. These planes may be perpendicular to the major axis of the end portion of the catheter. At least two additional electrodes may be provided adjacent at the ends of the major axis of the end portion. As a more specific example, the catheter may include four circumferences with eight electrodes spaced equiangularly on each circumference. Accordingly, in this specific implementation, the catheter may include at least 34 electrodes (32 circumferential and 2 end electrodes).

According to another example, an electrophysiological cardiac mapping system and technique based on a non-contact and non-expanded multi-electrode catheter may be implemented. Electrograms may be obtained with catheters having multiple electrodes (e.g., between 42 to 122 electrodes). According to this implementation, knowledge of the relative geometry of the probe and the endocardium may be obtained such as by an independent imaging modality such as transesophogeal echocardiography and/or 2D-, 3D-, or 4D-ICE. After the independent imaging, non-contact electrodes may be used to measure cardiac surface potentials and construct maps therefrom. This technique may include the following steps (after the independent imaging step): (a) measuring electrical potentials with a plurality of electrodes disposed on a probe positioned in the heart; (b) determining the geometric relationship of the probe surface and the endocardial surface; (c) generating a matrix of coefficients representing the geometric relationship of the probe surface and the endocardial surface; and (d) determining endocardial potentials based on the electrode potentials and the matrix of coefficients.

According to another example, a technique and apparatus for mapping the electrical potential distribution of a heart chamber may be implemented. An intra-cardiac multielectrode mapping catheter assembly may be inserted into a patient's heart. The mapping catheter assembly may include a multi-electrode array with an integral reference electrode, or, preferably, a companion reference catheter. The electrodes may be deployed in the form of a substantially spherical array. The electrode array may be spatially referenced to a point on the endocardial surface by the reference electrode or by the reference catheter which is brought into contact with the endocardial surface. The preferred electrode array catheter may carry a number of individual electrode sites (e.g., at least 24). Additionally, this example technique may be implemented with knowledge of the location of each of the electrode sites on the array, as well as a knowledge of the cardiac geometry. These locations are preferably determined by a technique of impedance plethysmography.

According to another example, a heart mapping catheter assembly may include an electrode array defining a number of electrode sites. The mapping catheter assembly may also include a lumen to accept a reference catheter having a distal tip electrode assembly which may be used to probe the heart wall. The mapping catheter may include a braid of insulated wires (e.g., having 24 to 64 wires in the braid), and each of the wires may be used to form electrode sites. The catheter may be readily positionable in a heart to be used to acquire electrical activity information from a first set of non-contact electrode sites and/or a second set of in-contact electrode sites.

According to another example, another catheter for mapping electrophysiological activity within the heart may be implemented. The catheter body may include a distal tip which is adapted for delivery of a stimulating pulse for pacing the heart or an ablative electrode for ablating tissue in contact with the tip. The catheter may further include at least one pair of orthogonal electrodes to generate a difference signal indicative of the local cardiac electrical activity adjacent the orthogonal electrodes.

According to another example, a process for measuring electrophysiologic data in a heart chamber may be implemented. The method may include, in part, positioning a set of active and passive electrodes into the heart, supplying current to the active electrodes, thereby generating an electric field in the heart chamber, and measuring the electric field at the passive electrode sites. The passive electrodes are contained in an array positioned on an inflatable balloon of a balloon catheter. In preferred embodiments, the array is said to have from 60 to 64 electrodes.

According to another example, cardiac mapping may be implemented using one or more ultrasound transducers. The ultrasound transducers may be inserted into a patient's heart and may collect a plurality of ultrasound slices (e.g., two dimensional or three-dimensional slices) at various locations and orientations within the heart. The location and orientation of a given ultrasound transducer may be known and the collected ultrasound slices may be stored such that they can be displayed at a later time. One or more ultrasound slices corresponding to the position of a probe (e.g., a treatment catheter) at the later time may be displayed and the probe may be overlaid onto the one or more ultrasound slices.

According to other examples, body patches and/or body surface electrodes may be positioned on or proximate to a patient's body. A catheter with one or more electrodes may be positioned within the patient's body (e.g., within the patient's heart) and the position of the catheter may be determined by a system based on signals transmitted and received between the one or more electrodes of the catheter and the body patches and/or body surface electrodes. Additionally, the catheter electrodes may sense biometric data (e.g., LAT values) from within the body of the patient (e.g., within the heart). The biometric data may be associated with the determined position of the catheter such that a rendering of the patient's body part (e.g., heart) may be displayed and may show the biometric data overlaid on a shape of the body part, as determined by the position of the catheter.

Figure 6A:
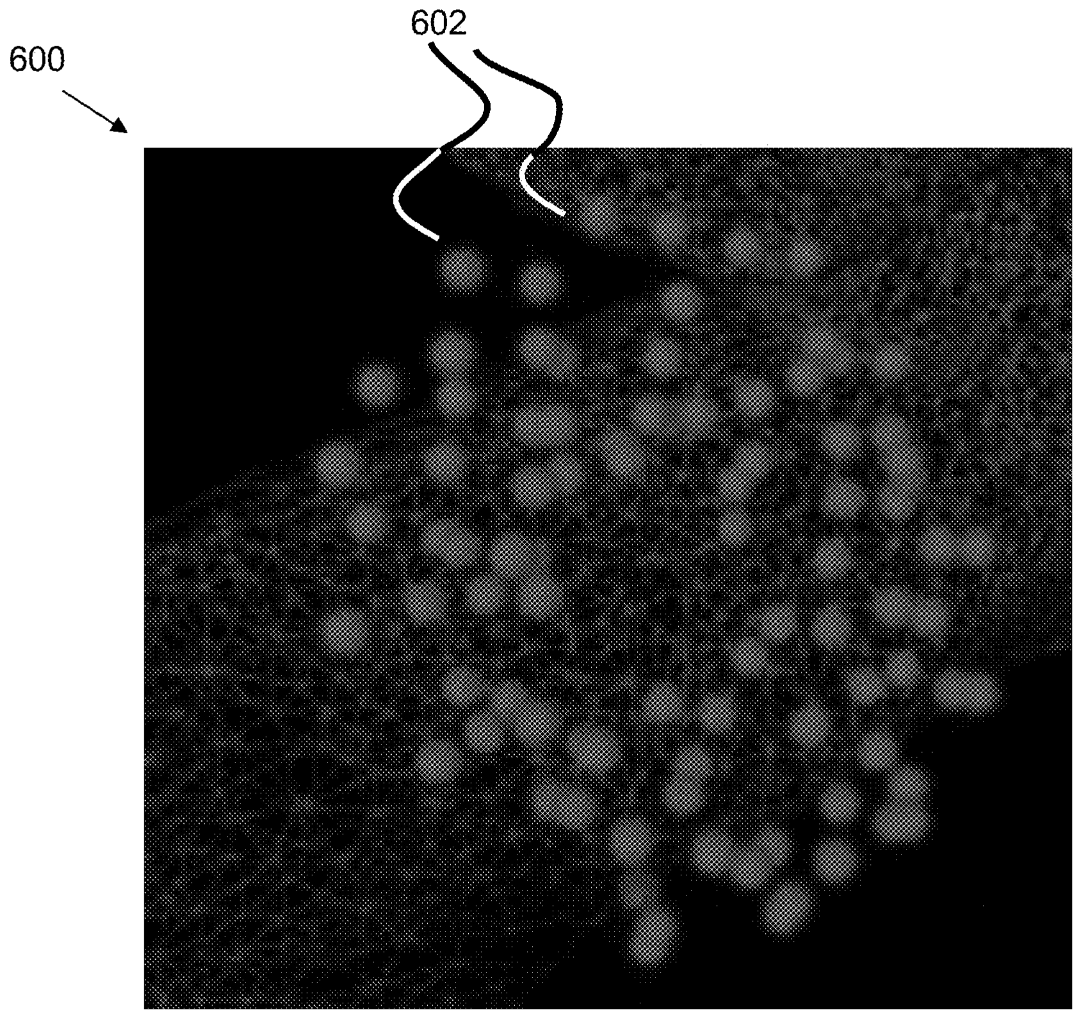
FIG. 6A is a screenshot of an example of a point cloud generated from a plurality of ablation sessions according to one or more embodiments.

As discussed above, some systems may illustrate or display the results of ablation sessions via a point cloud of marks or tags representing positions of each electrode during ablation across the plurality of sessions. FIG. 6A is a screenshot 600 of an example of such a point cloud generated from a plurality of ablation sessions according to one or more embodiments. Each tag 602, which may be variously referred to as a point, position, electrode position, mark, ablation tag, or by any other similar term, is represented by a red sphere or dot in the screenshot of FIG. 6A. In implementations using point clouds as shown in the example, it may be difficult for physicians to understand the effect of ablation session or sessions. For example, there is no clear indication of the ablation field energy received by the tissue. The energy from the electric field in between electrodes is not represented. There is no indication of accumulated energy on tissue due to repeated ablations. And there is no indication as to which tags were created during the same ablation session.

Figure 6B:
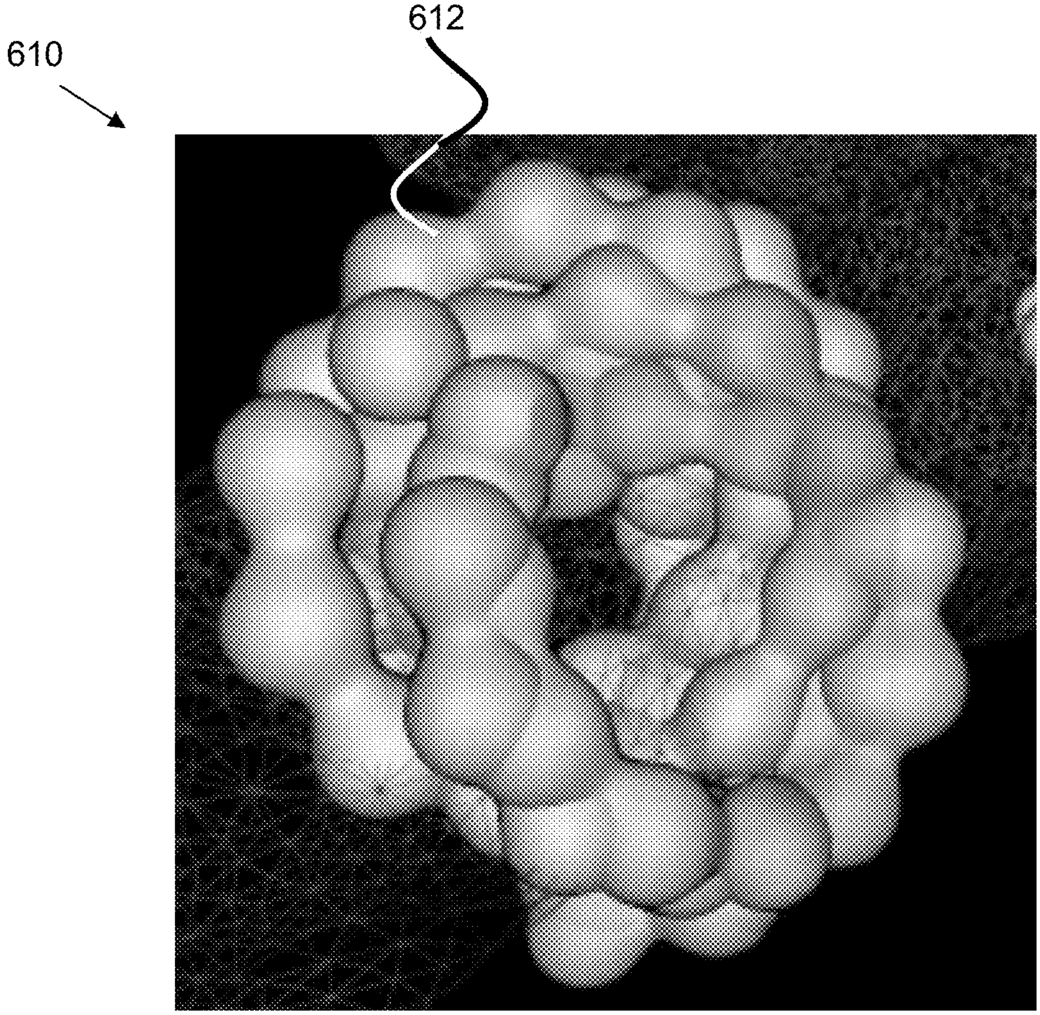
FIG. 6B is a screenshot of an example of a volumetric tracing of a plurality of implicit functions generated from a plurality of ablation sessions according to one or more embodiments.

By contrast, FIG. 6B is a screenshot 610 of an example of a volumetric tracing 612 of a plurality of implicit functions generated from a plurality of ablation sessions according to one or more embodiments. The implicit functions may include a signed distance function or other smoothing function based on positions of adjacent electrodes during an ablation session, resulting in a multi-lobed region or tube shape. In many implementations, the surface of the region may represent areas that received the same or similar amounts of energy during the ablation session. In some implementations, this may be determined via a signed distance function or any other similar smoothing function.

Figure 6C:
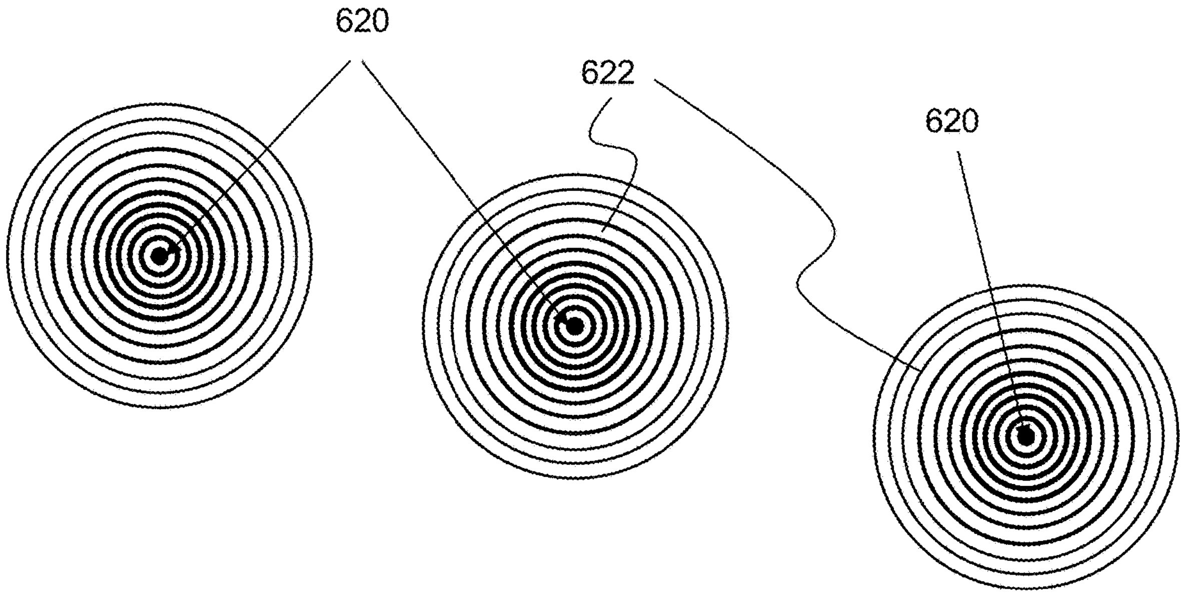
FIG. 6C is an illustration of example energy fields around a plurality of electrodes during an ablation session according to one or more embodiments.

For example, referring briefly to FIG. 6C, illustrated is an example of energy fields 622 around a plurality of electrodes 620 during an ablation session according to one or more embodiments. The energy fields 622 are shown as concentric circles, and represent an energy gradient or equal or approximately equal amounts of energy provided during ablation at a given distance. The energy at any particular distance from the electrode may be based on an inverse-square law; this is illustrated in FIG. 6C with thinner lines farther from each electrode 620. It may be understood that the illustration is for example purposes only and the thickness of the lines are not to scale or not proportionally representative of any particular energy level; it may be similarly understood that although only a few concentric circles are shown, ablation energy may extend further than shown.

Figure 6D:
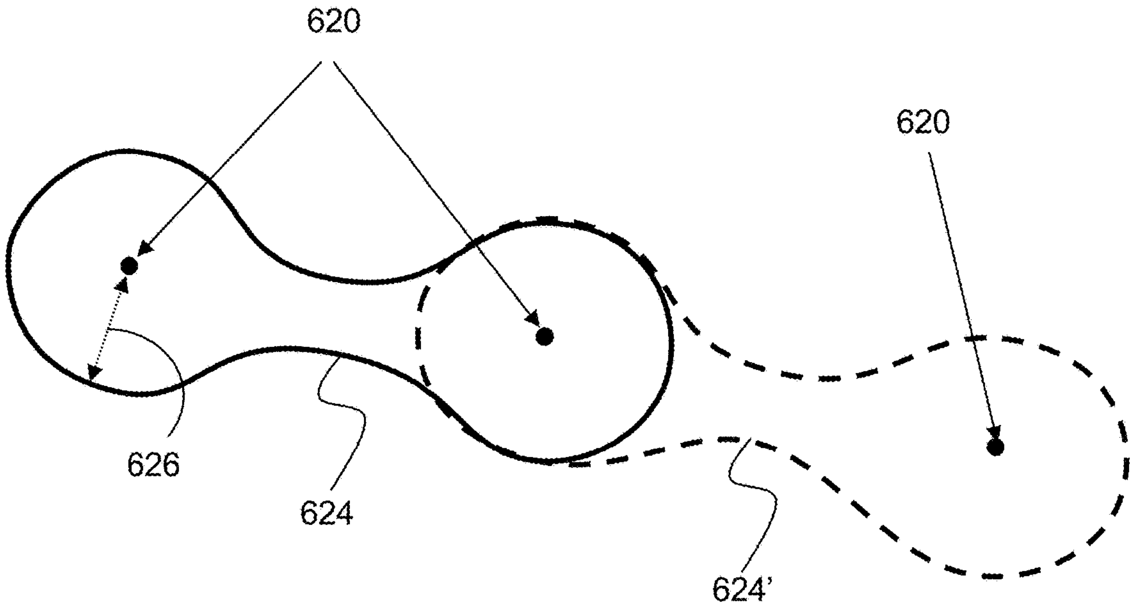
FIG. 6D is an illustration of example signed distance functions representing an energy field around the plurality of electrodes during the ablation session of FIG. 6C according to one or more embodiments.

FIG. 6D is an illustration of example signed distance functions 624 representing an energy field around the plurality of electrodes 620 during the ablation session of FIG. 6C according to one or more embodiments. For example, the boundary illustrated by function 624 represents a threshold distance from the left and middle electrodes, and the boundary illustrated by function 624' represents a threshold distance from the middle and right electrodes, with the boundary corresponding to an energy level received at that distance from the electrode(s). Accordingly, in many implementations, the boundary may also represent points around the electrodes retrieving similar or the same amount of energy. These functions may accordingly be combined into an aggregated implicit function to represent the areas accumulating the same energy during each ablation session. Although shown as a two-dimensional representation in FIGS. 6C and 6D, in many implementations, a three-dimensional environment may be utilized, and a three dimensional surface may be identified based on the implicit function. Additionally, while all three electrodes are shown as "active" in FIGS. 6C and 6D, in some implementations, an electrode may be inactive during an ablation session (e.g. disabled, not in contact with tissue, etc.). In some implementations, such inactive electrodes may be skipped during calculation of the implicit function.

The distance to boundaries 624, 624' (e.g. the threshold distance) may be dynamically configurable, set by a manufacturer or administrator, or otherwise varied. For example, a higher threshold will result in a thicker portion between the adjacent electrodes, while a lower threshold may result in a narrower portion or even a discontinuity. Varying this threshold may be useful for showing different accumulated energy levels in one or more ablation sessions.

Figure 6E:
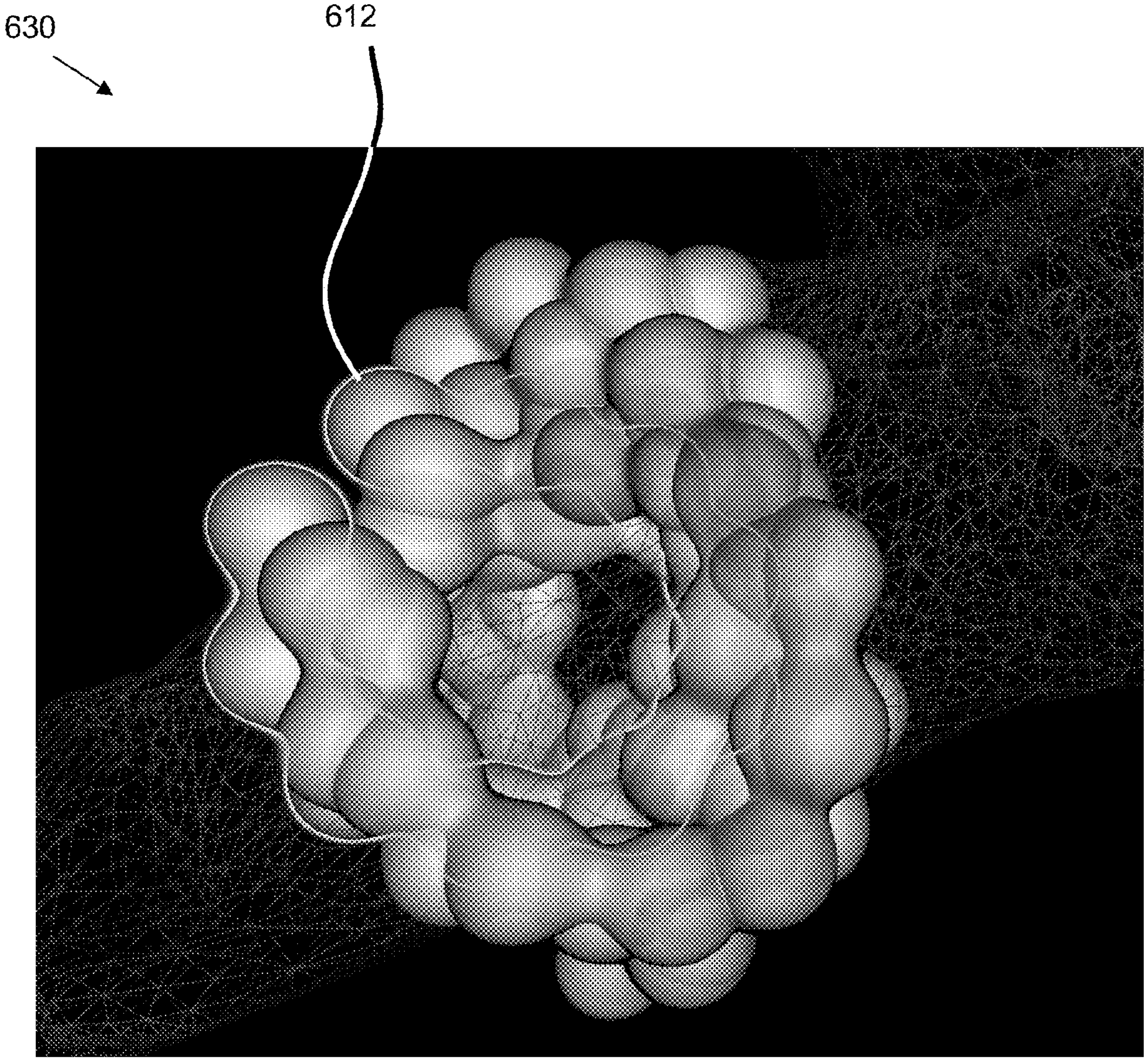
FIG. 6E is a screenshot of the example of volumetric tracing of a plurality of implicit functions of FIG. 6B with a highlighted implicit function corresponding to one ablation session of the plurality of ablation sessions, according to one or more embodiments.

As discussed above, each ablation session of a plurality of ablation sessions may be represented by an implicit function. The volumetric rendering of these sessions may accordingly be distinguished from other sessions in many implementations. For example, FIG. 6E is a screenshot 630 of an example of volumetric tracing of a plurality of implicit functions of FIG. 6B with a highlighted implicit function 632 (shown with highlighted border) corresponding to one ablation session of the plurality of ablation sessions, according to one or more embodiments.

In some implementations, to render the volumes represented by each implicit function, a system may subdivide a three-dimensional environment region into a plurality of voxels. Each voxel may be associated with the nearest electrode positions or active electrode positions during an ablation session, in some implementations. The system may calculate the implicit function and determine, for each voxel, whether the voxel is on (or within in some embodiments) the boundary of the volumetric surface. For example, the system may determine whether a distance to the nearest adjacent electrodes from the voxel is within a threshold, in some implementations. If so, a value for the voxel, representing a unit of accumulated energy may be incremented, modified, or adjusted according to an aggregation function. When rendering a volumetric surface for a subsequent ablation session, the voxel-associated values may be similarly incremented or adjusted. The accumulation of energy across sessions can be used by any arbitrary function such as a square or root of the sum of sessions on a voxel, in various implementations. For example, the aggregation function may include increasing a value representing accumulated energy for a voxel based on a distance to an electrode (or multiple electrodes). In some implementations, the aggregation function may be based on a time of ablation during the ablation session. Higher values for voxels are thus associated with positions that accumulated energy during a plurality of ablation sessions, or accumulated more total energy. As shown in the example screenshot of FIG. 6E, such voxels may be shaded or colored differently (e.g. darker in the embodiment illustrated, though other shadings or colorings are possible in other embodiments). In some implementations, transparency may be used (either alone or in addition to texture and/or color) to represent the accumulated energy, such that voxels with higher received energy may be less transparent than those with less energy received. These various implementations provide an intuitive and efficient visualization of the accumulated energy across a plurality of ablation sessions. A combination of the functions discussed above and/or other functions may be utilized in various implementations and may provide a smooth change in color and/or texture of the surface. Accordingly, as used herein, shading may be used to refer to any distinctive visual effect, including striping, stippling, hatching, cross-hatching, transparency, specularity, reflectivity, color, or any other type of visual modifier that can provide an indication of energy accumulation.

Figure 7:
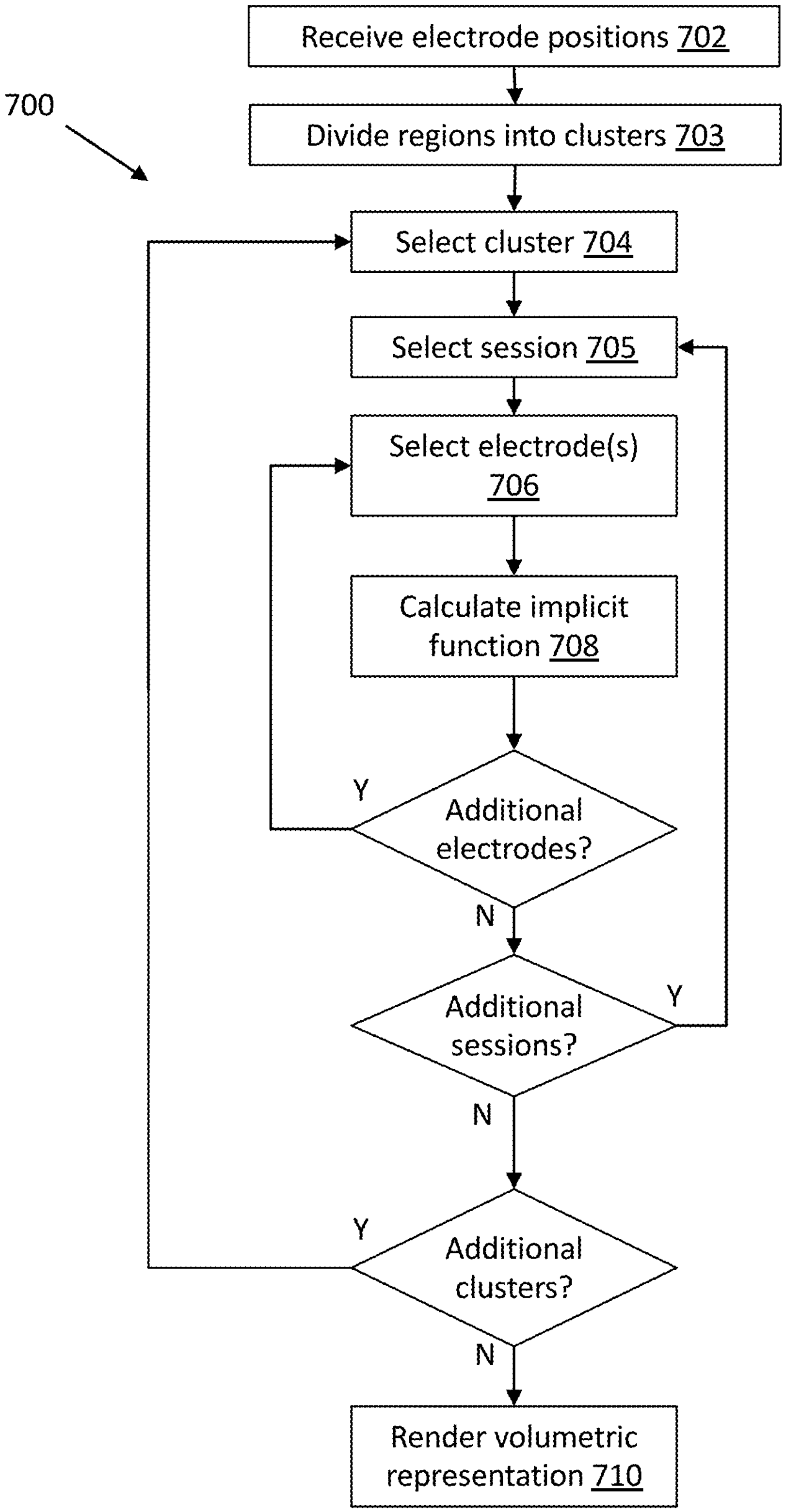
FIG. 7 is a flow chart of a method of visualization of pulsed field ablation tags, according to one or more embodiments.

Turning now to FIG. 7, a method 700 (e.g., performed by one or more processors of a computing device) of visualization of pulsed field ablation tags is illustrated according to one or more exemplary embodiments. The method 700 addresses a need of physicians to understand the effects of one or more ablation sessions in an easy and intuitive visual manner, and provides a high quality, highly efficient visualization with reduced processing resources required relative to high density arrays or bitmaps. The method begins at block 702, where one or more processors of the device may receive, from one or more sensors, positions of one or more electrodes of a catheter during an ablation session. The positions may be represented in any suitable format, such as by x, y, and z coordinates, spherical coordinates, indexes to voxels in an array, or any other such format. The catheter may be of any type and form, such as the linear, balloon, or loop catheters discussed above, and may include one electrode or more than one electrode. In various implementations, the sensors may comprise RF sensors, magnetic sensors, inductive sensors, or any other type and form of sensor or combination of sensors. Receiving the positions of the electrodes may comprise filtering noise or other motion (e.g. due to patient inhalation), identifying periods where the electrodes or catheter tip are not moving or have zero velocity, etc.

At block 703, in some implementations, the one or more processors may subdivide the electrodes and/or the region into a plurality of clusters, and at block 704, a cluster may be selected for processing. This may be done to reduce processing requirements for each cluster, for example, because farther away electrodes may have minimal effect. In some implementations, each cluster may include a subset of the plurality of electrodes. In some implementations, each cluster may include a subset of voxels of the three-dimensional environment. Clusters may be processed in parallel in many implementations, as they are independent; accordingly, in some implementations, block 704 may be performed for different clusters in parallel by different processors, services, appliances, or other computing devices. In other implementations, blocks 703-704 may be skipped.

At block 705, in some implementations, an ablation session may be selected from a plurality of sessions, and at block 706, in some implementations, the one or more processors may select a pair of electrodes from the plurality of electrodes, or select a pair of received positions (such as an adjacent pair of positions). In some implementations, the electrodes (or positions) may be selected responsive to their associated positions being in the same cluster. In other implementations, the electrodes (or positions) may be selected responsive to their associated positions being received from the same ablation session. In some implementations, each electrode may be associated with a semi-unique identifier or unique identifier. Points in the region or voxels may be associated with identifiers of electrodes that provided energy to the point or voxel during an ablation session with an amplitude or energy level above a threshold.

At block 708, in some implementations, the one or more processors may calculate an implicit function based on the positions of the selected pair of electrodes. In some implementations, the implicit function may comprise a smoothing function. In some implementations, the implicit function may comprise a signed distance function. In some implementations, the function may be further based on a predetermined threshold.

In some implementations, if there are additional electrodes, blocks 706-708 may be repeated iteratively. For example, in some implementations, the system may calculate a function for a first and second electrode or position, and then may select a third electrode position and calculate the function for the combination of the first and second electrode or position (e.g. the previously calculated function) and the newly selected electrode or position, thus iteratively building an aggregated function for all three electrodes or positions. In other implementations, blocks 706-708 may be repeated serially with pairs of electrodes or positions (e.g. calculating a distance function for a first and second electrode or position, then calculating a distance function for the second electrode or position and a third electrode or position, etc.). In such implementations, the system may avoid calculating energy contributed by the second electrode to any particular voxel twice. For example, as discussed above, in some implementations, a value associated with each voxel in a cluster may be incremented responsive to the voxel's position being within or on a boundary of a signed distance function for a first and second electrode or position. In some such implementations, when determining the effect of the second electrode or position and a newly selected third electrode or position, any voxel whose associated value was incremented may not have its value re-incremented. Put another way, in such implementations during calculation of the effect of any ablation session, a value associated with a voxel may only be incremented once regardless of how many adjacent electrodes' effects are applied. In other implementations, such as when building an aggregated function as discussed above, the value associated with a voxel may be incremented multiple times.

In many implementations, blocks 705-708 may be repeated for additional ablation sessions. Although shown repeating prior to block 710, in some implementations, blocks 705-710 may be repeated (e.g. the loop may occur after a first instance of block 710, and block 710 may be repeated for each additional session). Similarly, in many implementations, blocks 704-708 may be repeated for additional clusters of electrode positions within the environment. In many implementations, blocks 704-708 may be performed for different clusters in parallel by separate processors, services, or devices.

At block 710, a volumetric representation of the calculated implicit function (or functions for multiple ablation sessions) may be rendered. As discussed above, in many implementations, the system may determine a value associated with each voxel in a cluster or three-dimensional environment, the value incremented responsive to the voxel being within (or on the boundary of, in various implementations) a signed distance function for a pair of adjacent electrodes or corresponding positions. In some implementations, the unique or semi-unique identifier of an electrode or electrodes that are associated with the corresponding boundary may be stored with or associated with the voxel; this may be in addition to or in place of an energy value or other counter, in various implementations. For example, responsive to determining that a voxel is within (or on) a boundary according to a signed distance function or other smooth function, the identifiers of associated electrodes may be stored in association with the voxel, such that the voxel includes or is associated with a set of identifiers of electrodes and their positions during an ablation session. This enables the system to calculate the distance to the boundary at runtime at high visual fidelity without the need to store additional data about the boundary surface. In some implementations, the system may shade, color, make visible, or otherwise highlight or show each voxel with an incremented value to display the volumetric representation. In other implementations, the representation may be rendered via ray tracing using the boundary of the implicit function as a reflective surface. Other implementations of rendering may be utilized as needed. The volumetric representation may be rendered to a display, such as a monitor, a stereoscopic display (e.g. virtual reality or augmented reality display or glasses), a volumetric display, a holographic display, a pseudo-three dimensional display (e.g. a two dimensional display with head tracking and rendering of a pseudo-three dimensional environment), or any other suitable display.

As discussed above, at block 710, the system may utilize the electrode positions and calculated functions to generate volumetric representations of the ablation session or sessions. Such implementations are important because otherwise it may be difficult to distinguish tags within the scattered point clouds generated during each session. In particular, it may be hard or impossible to assess the number of ablations performed in a specific location, which may be a particularly important factor for determining the quality of ablation. The point cloud may also provide a poor representation of the ablation field energy received by the tissue (the energy between two electrodes is not represented well). Furthermore, the point cloud may provide no indication of the accumulated energy on tissue affected by more than one ablation session.

Figure 8B:
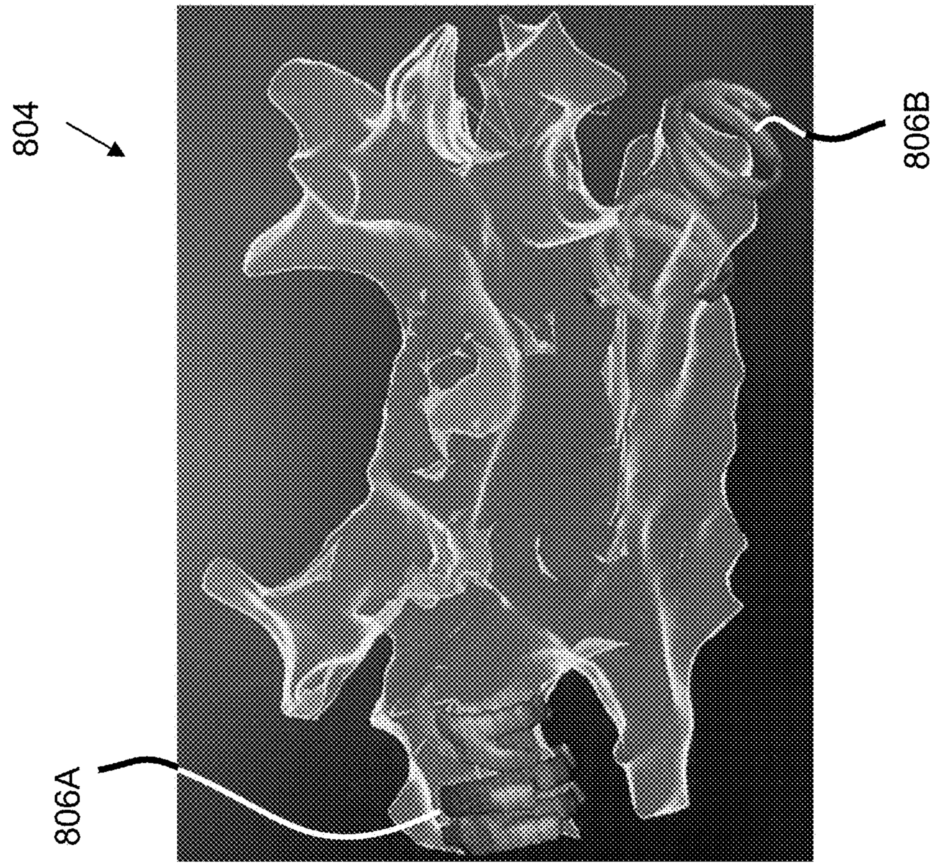
FIGS. 8A and 8B are screenshots of an example of point clouds and volumetric tracing, respectively, generated from a plurality of ablation sessions, according to one or more embodiments.
Figure 8A:
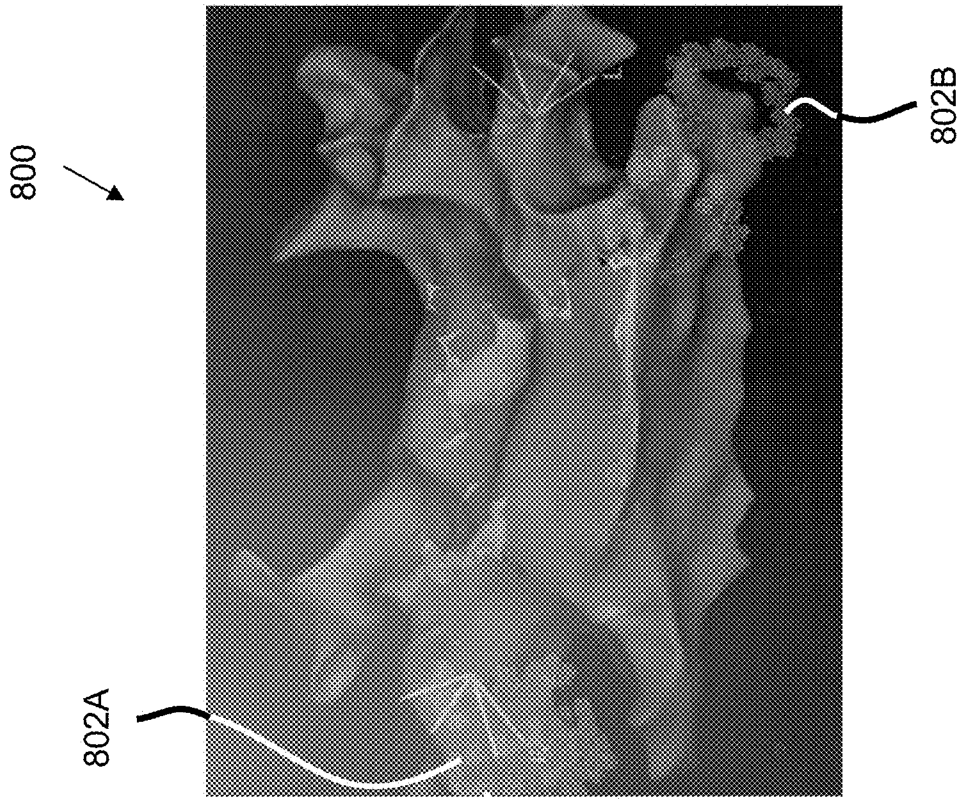

For example, FIG. 8A is a screenshot 800 of an example of point clouds 802A, 802B generated from a plurality of ablation sessions, according to one or more embodiments. As shown, the point clouds 802A, 802B consist of a large number of ablation tags corresponding to positions of the electrodes during a plurality of ablation sessions. By contrast, FIG. 8B is a screenshot 804 of an example of volumetric representations 806A, 806B generated from the point clouds 802A, 802B, according to some implementations. Unlike the point clouds of FIG. 8A, the volumetric representations allow the user to distinguish between separate ablation sessions and identify the positional relationships between the tags in three-dimensional space.

Figure 8C:
FIG. 8C is an illustration of an example of ablation tags in a three-dimensional space, according to one or more embodiments.
Figure 8D:
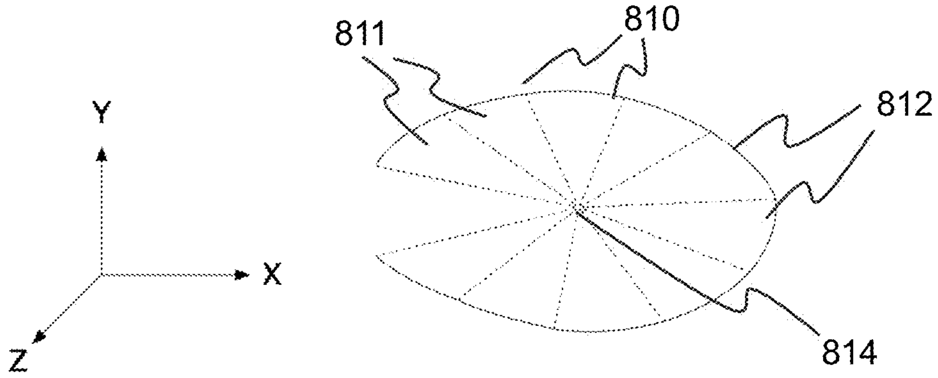
FIG. 8D is an illustration of an example of a traced path between the ablation tags in the three-dimensional space of FIG. 8C, according to one or more embodiments.
Figure 8E:
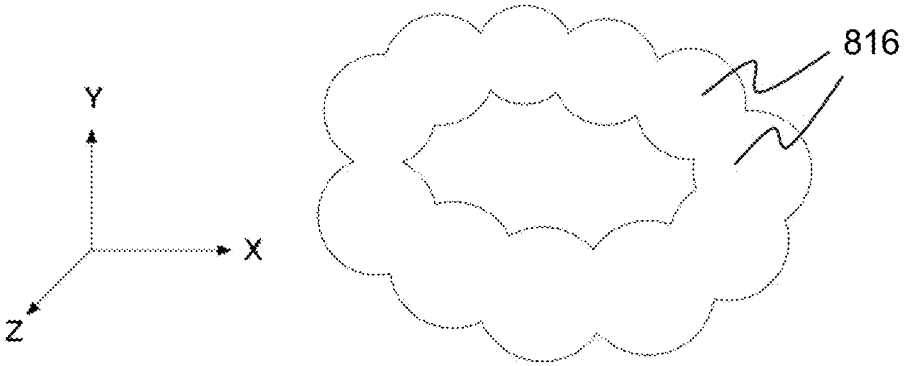
FIGS. 8E and 8F are illustrations of an example of volumetric tracing of a plurality of implicit functions in a three-dimensional space from different viewing angles, according to one or more embodiments.

FIGS. 8C-8E illustrate one implementation of how these volumetric representations may be generated. Starting with FIG. 8C, illustrated is a representation of a plurality of ablation tags 810 in a three-dimensional space, according to one or more embodiments. The ablation tags 810 are shown as stars for clarity, but may be represented by points, voxels, polygons, or any other shape. In some implementations, a centroid 814 of the tags 810 may be identified (sometimes referred to as a volumetric site center, tag center, tag centroid, ablation session center, or by similar terms), and a path 812 may be traced through each tag 810, creating a plurality of wedge shaped segments 811, as shown in FIG. 8D. The path 812 (and wedges 811) may then be expanded orthogonally to the path 812 with a plurality of voxels to represent the ablation energy, time, number of discrete ablation sessions providing energy to a particular voxel (e.g. as an incrementing sum of sessions providing energy for each voxel), or other characteristics. For example, the path 812 may be represented by line of small voxels. Neighboring voxels may be added to the path, expanding the line orthogonally (e.g. laterally, medially, etc.) with a number of voxels added dependent on ablation energy, ablation time, or settings by a user or physician. For example, in one such implementation, the path may be expanded by five voxels laterally in each direction based on an ablation of duration x and ten voxels laterally in each direction based on an ablation of duration 2×. The expansion need not be linear, and may be based on any suitable formula (e.g. geometric, exponential, etc.). As one non-limiting example, a marching cube (e.g. as discussed in U.S. Pat. No. 4,710,876, incorporated by reference herein) or similar algorithm (e.g. marching tetrahedra, or any other implicit surface rendering algorithm, etc.) may be applied to determine a smoothed surface 816, as shown in the example implementation of FIG. 8E. For example, each voxel may be replaced with a polygon or polygons from a predetermined set of polygons needed to represent the part of an isosurface (i.e. smoothed surface 816) that passes through the voxel.

Figure 8F:
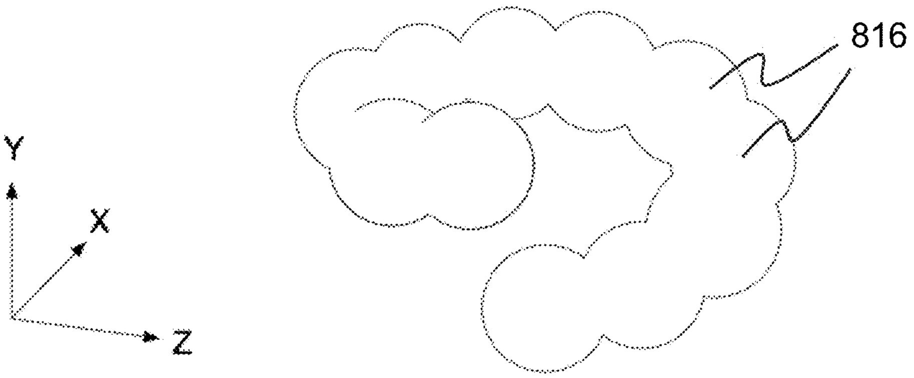
Figure 8G:
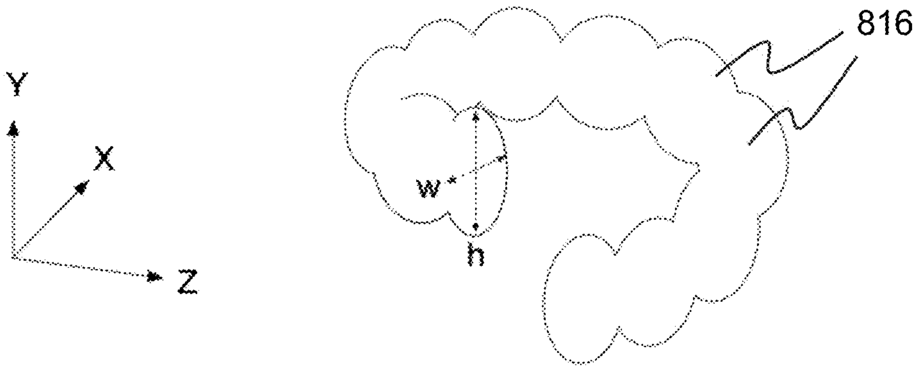
FIG. 8G is an illustration of an example of volumetric tracing with adjustable function parameters, according to one or more embodiments.

However, in FIG. 8E, the example volumetric representation 816 appears to be closed or a complete loop. This may be misleading, depending on the viewing angle. By utilizing a three-dimensional representation and allowing re-orientation of the representation 816 and/or the camera or viewpoint, a physician or other user may inspect the volumetric representation from multiple angles to identify gaps. For example, FIG. 8F shows the example volumetric representation 816 of FIG. 8E from an alternate, rotated angle, according to some embodiments. The previously hidden gap between the ends of the ablation path can be more easily seen. Furthermore, as mentioned above, when expanding the path into voxels, parameters such as time and energy may be used to determine the height and width of the resulting volume. These parameters may be configured by a manufacturer or administrator of the system, or may be dynamically modified by a user or physician. For example, as shown in the illustration of FIG. 8G, a narrower width may be utilized to more readily visualize the gap between the ablation regions. This may be particularly beneficial with multiple overlapping ablation sessions, in which thinner "ribbons" may allow for identification of small gaps. In some implementations, the width and height may be separately adjusted, while in other implementations, the volumes may be cylindrical or spherical, and a radius of the volumes may be adjusted, modifying both the width and height accordingly.

Figure 9:
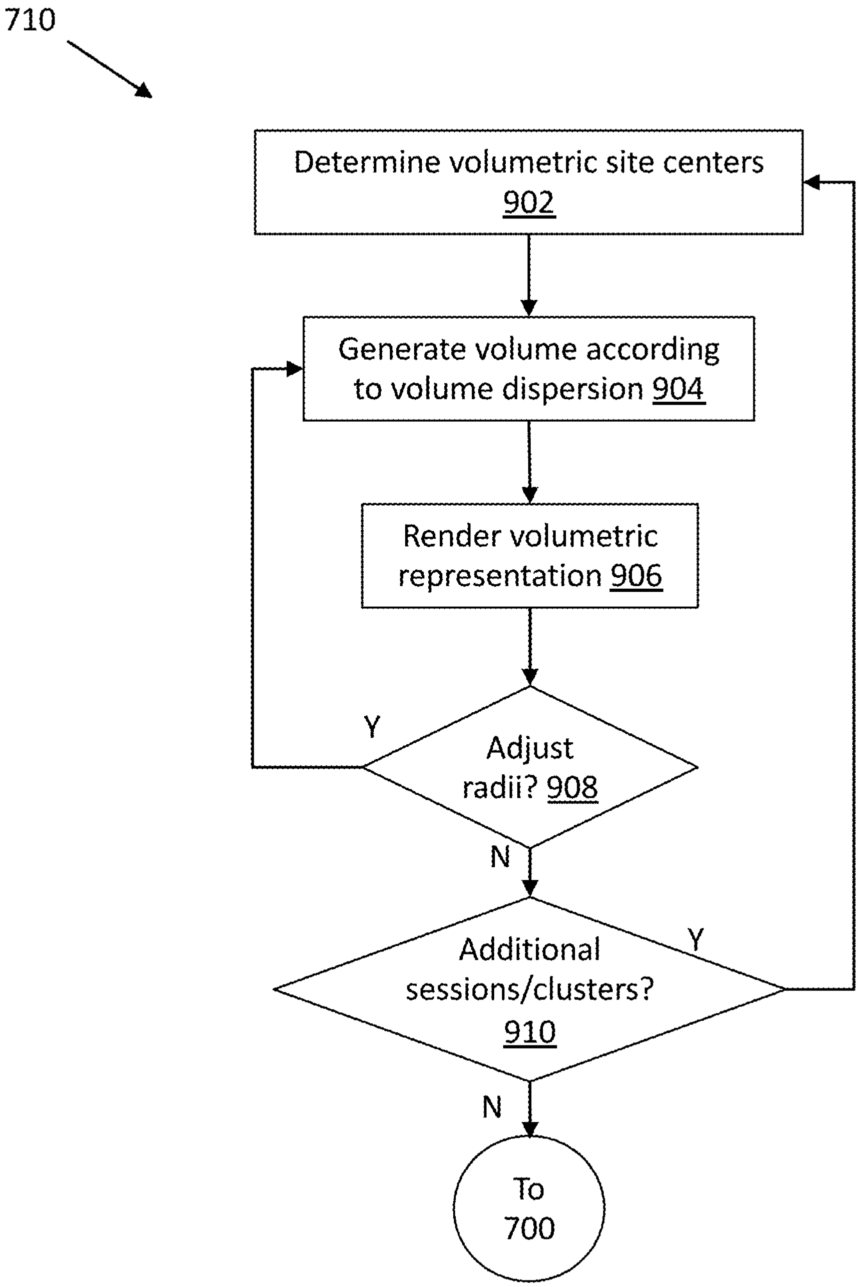
FIG. 9 is a flow chart of a method of rendering volumetric tracing generated from a plurality of ablation sessions, according to one or more embodiments.

FIG. 9 is a flow chart of an example method of rendering volumetric tracing generated from a plurality of ablation sessions as discussed above in connection with block 710, according to one or more embodiments.

At block 902, in some implementations, the system may determine one or more ablation session centers or volumetric site centers. As discussed above, a volumetric site center may comprise a centroid of positions of ablation tags during a single session, in some implementations. In some implementations, and as discussed above in connection with FIGS. 8C and 8D, the ablation tags 810 may naturally follow a two-dimensional path 812 within the three-dimensional environment. In some such implementations, the volumetric site center or centroid 814 may be determined as a two dimensional centroid 814 from positions of ablation tags 810, with a common plane of the ablation tags 810. In other implementations, the path 813 may follow a helix or spiral path in three dimensions. In many implementations, each tag may have a position in the three-dimensional space, and accordingly, the centroid may be calculated as an average of the coordinates of each point (e.g. c=average($x_1$:$x_n$), average ($y_1$:$y_n$), average($z_1$:$z_n$)). In other implementations, a median or a middle of extrema may be used to find the centroid. These may result in different centroids, and accordingly, the particular formula used may be dependent on the implementation or the type of catheter.

At block 904, in some implementations, a volume 816 may be generated according to a volume dispersion. In some implementations, this may include generating a central path 812 along the ablation tags 810 around the centroid 814. The central path 812 may be represented by a string or formation of connected voxels. For example, in some implementations, given the centroid, a first tag and a second tag, an arc may be determined between the first tag and second tag along the path 812. As discussed above, in many implementations, the centroid 814 and each tag 810 may be associated with three-dimensional coordinates within the environment, and the arc may be calculated using these three-dimensional coordinates. For example, in one such implementation, a radius r may be calculated based on a distance from the centroid 814 to each of two neighboring ablation tags 810 (e.g. as an average of the Euclidean distance between each tag and the centroid in three dimensions). Then, given the determined radius, centroid, and the tags as starting and ending points along the circumference of a circle of radius r with an origin at the centroid, an arc segment may be calculated (for example, given a plane containing the start, end, and centroid points, the system may identify a unit vector in the plane from the centroid to the start point as x', identify an orthogonal unit vector in the plane as y', and calculate a portion of a circle f(t)=r cos(t)x'+r sin(t)y' with t equal to the angle between vectors from the centroid to each tag). In other implementations, Bezier or spline curves may be calculated (e.g. using tangent lines at each of the starting and ending ablation tags that are orthogonal to the vector from the centroid to the corresponding tag, etc.). Voxels along the determined path 812 may be included in the path.

For volume dispersion, in some implementations, the system may calculate, for each voxel within the environment, a distance from the voxel to each tag 810 and the calculated path 812 (or voxels of the path 812, as discussed above). If the distance is below a threshold, in some implementations, the voxel may be included in the volume. In other implementations, the calculated path 812 may be expanded as discussed above (e.g. by including a given number of neighboring voxels in the volume based on a configured height or width of the volume).

At block 906, in some implementations, a volumetric representation 816 of the path 812 may be rendered. Rendering the volumetric representation 816 may include expanding the voxels of the central path 812 according to ablation characteristics as discussed above in connection with FIG. 8D, such as cumulative energy deposited, total ablation time, number of discrete ablation sessions providing energy to a particular voxel (e.g. as an incrementing sum of sessions providing energy for each voxel), etc., and/or parameters set by a user or physician, such as a visualization radius, height, width, or filter threshold for any of the above parameters. As discussed above, in some implementations, the path 812 may be represented by line of small voxels. Neighboring voxels may be added to the path, expanding the line orthogonally (e.g. laterally, medially, etc.) with a number of voxels added dependent on ablation energy, ablation time, or settings by a user or physician. For example, a physician or user may set a minimum energy threshold and voxels associated with deposited energy below the threshold may not be included in the rendering. As discussed above, once the voxels have been identified, a surface for the volume may be determined, e.g., via a marching cube, ball pivoting algorithm (BPA), or a fast anatomical mapping (FAM) algorithm. For example, the system may generate a polygonal mesh of the surface by identifying three points or voxels intercepted by a three dimensional sphere or ball of a given diameter, generating a surface triangle from those three points, and then repeating the process starting from an edge of the triangle. Once a surface boundary has been determined, a distance field may be generated and the volume ray traced.

As discussed above, the various parameters, including filtering or visualization parameters, may be adjusted at block 908 and blocks 904-906 repeated. Additionally, blocks 902-906 may be repeated at block 910 for additional ablation sessions or clusters of ablation tags in the environment. The result may then be displayed to the user. In many implementations, the user or physician may then perform further modifications or edits to the visualization parameters, and the result re-rendered, including rotations, repositioning of a virtual camera or viewpoint, scaling, filtering, or other such functions.

Accordingly, embodiments of the systems and methods discussed herein provide for an intuitive and easily understandable visualization of the effect of one or more ablation sessions on tissue, with reduced processing or resource consumption relative to array-based implementations via the use of implicit functions, and particularly signed distance functions calculated based on positions of adjacent electrodes of a catheter during ablation.

Although features and elements are described above in particular combinations, one of ordinary skill in the art will appreciate that each feature or element can be used alone or in any combination with the other features and elements. In addition, the methods described herein may be implemented in a computer program, software, or firmware incorporated in a computer-readable medium for execution by a computer or processor. Examples of computer-readable media include electronic signals (transmitted over wired or wireless connections) and computer-readable storage media. Examples of computer-readable storage media include, but are not limited to, a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs). A processor in association with software may be used to implement a radio frequency transceiver for use in a WTRU, UE, terminal, base station, RNC, or any host computer.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although features and elements are described above in particular combinations, one of ordinary skill in the art will appreciate that each feature or element can be used alone or in any combination with the other features and elements. In addition, the methods described herein may be implemented in a computer program, software, or firmware incorporated in a computer-readable medium for execution by a computer or processor. A computer readable medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire Examples of computer-readable media include electrical signals (transmitted over wired or wireless connections) and computer-readable storage media. Examples of computer-readable storage media include, but are not limited to, a register, cache memory, semiconductor memory devices, magnetic media such as internal hard disks and removable disks, magneto-optical media, optical media such as compact disks (CD) and digital versatile disks (DVDs), a random access memory (RAM), a read-only memory (ROM), an erasable programmable read-only memory (EPROM or Flash memory), a static random access memory (SRAM), and a memory stick. A processor in association with software may be used to implement a radio frequency transceiver for use in a terminal, base station, or any host computer.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The descriptions of the various embodiments herein have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system for visualization of pulsed field ablation tags, comprising:

a device, comprising a processor in communication with one or more sensors and a catheter comprising a plurality of electrodes; and wherein the processor is configured to:

receive, via the one or more sensors, a position of each of the plurality of electrodes within a three-dimensional environment during a plurality of ablation sessions, calculate, for each ablation session, a first implicit function representing an energy field of the corresponding ablation session from the received positions of each of the plurality of electrodes for the corresponding ablation session, wherein the first implicit function is calculated via a signed distance function based on positions of a pair of adjacent electrodes of the plurality of electrodes during the corresponding ablation session, identify an intersection of the calculated energy fields for the plurality of ablation sessions corresponding to regions having a number of ablation applications exceeding a threshold; and present, via a display, a first volumetric representation of the identified intersection of the calculated energy fields.

2. The system of claim 1, wherein the processor is further configured to calculate the first implicit function via a plurality of signed distance functions, each corresponding to a different pair of adjacent electrodes.

3. The system of claim 1, wherein each electrode of the plurality of electrodes is associated with a unique identifier; and wherein the processor is further configured to determine, for each voxel of a plurality of voxels of the three dimensional environment, one or more identifiers of electrodes that provided energy to a position corresponding to the voxel during each ablation session.

4. The system of claim 1, wherein the processor is further configured to, for each of a plurality of voxels of the three-dimensional environment, calculate a distance from the voxel to a position of an electrode of the plurality of electrodes.

5. The system of claim 4, wherein the processor is further configured to, for each of the plurality of voxels of the three-dimensional environment, determine whether the corresponding calculated distance is less than a threshold.

6. The system of claim 5, wherein the processor is further configured to, for one or more voxels of the plurality of voxels of the three-dimensional environment, modify a value associated with the voxel responsive to the corresponding calculated distance being less than the threshold.

7. The system of claim 5, wherein the processor is further configured to modify a value associated with a first voxel, responsive to the distance from the first voxel to a position of an electrode of the plurality of electrodes during the corresponding ablation session being less than the threshold; and modify the value associated with the first voxel, responsive to the distance from the first voxel to a position of an electrode of the plurality of electrodes during a different ablation session being less than the threshold.

8. The system of claim 5, wherein the processor is further configured to present the first volumetric representation as one or more voxels in the three-dimensional environment, each voxel shaded based on a value associated with the voxel.

9. The system of claim 1, wherein the processor is further configured to:

determine a centroid of the received positions for each ablation session; and construct a central path around the determined centroid for each ablation session.

10. The system of claim 1, wherein the processor is further configured to:

sort the positions of each of the plurality of electrodes during each ablation session into a plurality of clusters; and calculate, for each ablation session, the first implicit function via a signed distance function between pairs of electrodes within each cluster.

11. A method for visualization of pulsed field ablation tags, comprising:

receiving, by a processor of a device from one or more sensors, a position within a three-dimensional environment of each of a plurality of electrodes of a catheter during a plurality of ablation sessions;

calculating, by the processor for each ablation session, a first implicit function representing an energy field of the corresponding ablation session from the received positions of each of the plurality of electrodes for the corresponding ablation session, wherein the first implicit function is calculated via a signed distance function based on positions of a pair of adjacent electrodes of the plurality of electrodes during the corresponding ablation session;

identifying an intersection of the calculated energy fields for the plurality of ablation sessions corresponding to regions having a number of ablation applications exceeding a threshold; and presenting, by the processor via a display, a first volumetric representation of the identified intersection of the calculated energy fields.

12. The method of claim 11, further comprising calculating the first implicit function via a plurality of signed distance functions, each corresponding to a different pair of adjacent electrodes.

13. The method of claim 11, wherein each electrode of the plurality of electrodes is associated with a unique identifier; and further comprising determining, for each voxel of a plurality of voxels of the three dimensional environment, one or more identifiers of electrodes that provided energy to a position corresponding to the voxel during the corresponding ablation session.

14. The method of claim 11, further comprising calculating, for each of a plurality of voxels of the three-dimensional environment, a distance from the voxel to a position of an electrode of the plurality of electrodes.

15. The method of claim 14, further comprising determining, for each of the plurality of voxels of the three-dimensional environment, whether the corresponding calculated distance is less than a threshold.

16. The method of claim 15, further comprising, for one or more voxels of the plurality of voxels of the three-dimensional environment, modifying a value associated with the voxel responsive to the corresponding calculated distance being less than the threshold.

17. The method of claim 15, further comprising modifying a value associated with a first voxel, responsive to the distance from the first voxel to a position of an electrode of the plurality of electrodes during the corresponding ablation session being less than the threshold; and modifying the value associated with the first voxel, responsive to the distance from the first voxel to a position of an electrode of the plurality of electrodes during a different ablation session being less than the threshold.

18. The method of claim 15, further comprising presenting, by the processor, the first volumetric representation as one or more voxels in the three- dimensional environment, each voxel shaded based on a value associated with the voxel.

* * * * *